US 10,201,935 B2

(12) United States Patent
Augustine et al.

(10) Patent No.: US 10,201,935 B2
(45) Date of Patent: Feb. 12, 2019

(54) ELECTRIC HEATING PAD

(71) Applicant: Augustine Temperature Management LLC, Eden Prairie, MN (US)

(72) Inventors: Scott D. Augustine, Deephaven, MN (US); Randall C. Arnold, Minnetonka, MN (US); Ryan S. Augustine, Minneapolis, MN (US); Rudolf A. Deibel, Eden Prairie, MN (US); Scott A. Entenman, Saint Paul, MN (US); Garrett J. Augustine, Deephaven, MN (US); Brent M. Augustine, Minneapolis, MN (US)

(73) Assignee: Augustine Temperature Management LLC, Eden Prairie, MN (US)

( * ) Notice: Subject to any disclaimer, the term of this patent is extended or adjusted under 35 U.S.C. 154(b) by 0 days.

(21) Appl. No.: 14/842,533

(22) Filed: Sep. 1, 2015

(65) Prior Publication Data

US 2015/0373781 A1    Dec. 24, 2015

Related U.S. Application Data

(63) Continuation of application No. 14/287,292, filed on May 27, 2014, which is a continuation of application
(Continued)

(51) Int. Cl.
*B29C 65/48* (2006.01)
*H05B 3/34* (2006.01)
(Continued)

(52) U.S. Cl.
CPC .............. *B29C 65/48* (2013.01); *A61B 18/16* (2013.01); *A61F 7/007* (2013.01); *A61F 7/08* (2013.01);
(Continued)

(58) Field of Classification Search
CPC ... B29C 65/48; A61B 18/16; A61B 2018/167; A61F 7/007; A61F 7/08; A61F 7/0097;
(Continued)

(56) References Cited

U.S. PATENT DOCUMENTS 2,403,676 A    7/1946   Modlinski
2,497,186 A    2/1950   Pedersen
(Continued)

FOREIGN PATENT DOCUMENTS

DE    3343664 C1    3/1985
DE    10065592 A1   7/2002
(Continued)

OTHER PUBLICATIONS

International Search Report and the Written Opinion of the International Searching Authority, or the Declaration for International Pat. App. No. PCT/US2015/025374, Nov. 9, 2015, 15 pages, European Patent Office, Rijswijk, The Netherlands.
(Continued)

*Primary Examiner* — Shawntina Fuqua
(74) *Attorney, Agent, or Firm* — Fredrikson & Byron, P.A.

(57) ABSTRACT

An electric heating pad for warming a patient. The electric heating pad may be a heated underbody support, heated mattress or heated mattress overlay. An embodiment of the heating pad includes a flexible sheet-like heating element including an upper edge, a lower edge, and at least two side edges. The heating pad may also include a shell covering the heating element and comprising at least two sheets of flexible material (e.g., two sheets may be one sheet folded over to form at least two sheets). The two sheets of flexible material may be coupled together about the edges of the heating element by a weld. The material of the two sheets may include urethane. In some embodiments, a catalyst to
(Continued)

accelerate hydrogen peroxide decomposition is coated on or impregnated into an element within the shell, or on the interior surface of the shell.

47 Claims, 28 Drawing Sheets

Related U.S. Application Data

No. 13/460,368, filed on Apr. 30, 2012, now Pat. No. 8,772,676, which is a continuation of application No. 12/050,806, filed on Mar. 18, 2008, now Pat. No. 8,283,602, application No. 14/842,533, which is a continuation-in-part of application No. 14/683,915, filed on Apr. 10, 2015, and a continuation-in-part of application No. 13/422,279, filed on Mar. 16, 2012, now abandoned.

(60) Provisional application No. 60/895,736, filed on Mar. 19, 2007, provisional application No. 62/079,076, filed on Nov. 13, 2014.

(51) Int. Cl.
| | | |
|---|---|---|
| B23K 20/10 | (2006.01) | |
| B23K 20/22 | (2006.01) | |
| B23K 13/00 | (2006.01) | |
| H05B 1/02 | (2006.01) | |
| H05B 3/14 | (2006.01) | |
| A61F 7/00 | (2006.01) | |
| A61F 7/08 | (2006.01) | |
| A61B 18/16 | (2006.01) | |

(52) U.S. Cl.
CPC ............ *B23K 13/00* (2013.01); *B23K 20/10* (2013.01); *B23K 20/22* (2013.01); *H05B 1/0272* (2013.01); *H05B 3/145* (2013.01); *H05B 3/146* (2013.01); *H05B 3/342* (2013.01); *H05B 3/347* (2013.01); *A61B 2018/167* (2013.01); *A61F 2007/0093* (2013.01); *A61F 2007/0096* (2013.01); *H05B 2203/011* (2013.01); *H05B 2203/016* (2013.01); *H05B 2203/033* (2013.01)

(58) Field of Classification Search
CPC ...... A61F 2007/0093; A61F 2007/0096; A61F 2007/0071; B23K 13/00; B23K 20/10; B23K 20/22; H05B 1/0272; H05B 3/145; H05B 3/146; H05B 3/342; H05B 3/347; H05B 3/34; H05B 3/36; H05B 2203/011; H05B 2203/016; H05B 2203/033
See application file for complete search history.

(56) References Cited

U.S. PATENT DOCUMENTS

| | | |
|---|---|---|
| 2,706,768 A | 4/1955 | Kaplan |
| 2,715,674 A | 8/1955 | Abbott |
| 3,008,152 A | 11/1961 | Seidenberg |
| 3,134,891 A | 5/1964 | Hyer |
| 3,137,871 A | 6/1964 | Florio |
| 3,340,549 A | 9/1967 | Billerbeck |
| 3,380,087 A | 4/1968 | Petty et al. |
| 3,582,456 A | 6/1971 | Stolki |
| 3,634,655 A | 1/1972 | Jordan |
| 3,690,325 A | 9/1972 | Kenny |
| 3,780,262 A | 12/1973 | Rudd |
| 3,808,403 A | 4/1974 | Gunma |
| 3,839,621 A | 10/1974 | Hariu |
| 3,854,156 A | 12/1974 | Williams |
| 3,874,504 A | 4/1975 | Verakas |
| 3,900,654 A | 8/1975 | Stinger |
| 3,936,661 A | 2/1976 | Furuishi |
| 4,061,898 A | 12/1977 | Murray |
| 4,118,531 A | 10/1978 | Hauser |
| 4,149,066 A | 4/1979 | Niibe |
| 4,186,294 A | 1/1980 | Bender |
| 4,250,398 A * | 2/1981 | Ellis .................... B32B 7/02 219/528 |
| 4,270,040 A * | 5/1981 | McMullan ............ H05B 3/36 219/212 |
| 4,363,947 A | 12/1982 | Bergersen et al. |
| 4,423,308 A | 12/1983 | Callaway |
| 4,479,795 A | 10/1984 | Mustacich |
| 4,495,402 A | 1/1985 | Burdick |
| 4,534,886 A * | 8/1985 | Kraus ................... B29C 70/504 252/502 |
| 4,626,664 A | 12/1986 | Grise |
| 4,658,119 A | 4/1987 | Endo et al. |
| 4,660,388 A | 4/1987 | Greene, Jr. |
| 4,661,689 A | 4/1987 | Harrison |
| 4,676,247 A | 6/1987 | Van Cleve |
| 4,682,447 A | 7/1987 | Osborn |
| 4,691,762 A | 9/1987 | Elkins et al. |
| 4,719,335 A | 1/1988 | Batliwalla |
| 4,747,409 A | 5/1988 | Silen |
| 4,764,665 A | 8/1988 | Orban |
| 4,798,936 A | 1/1989 | Johnson |
| 4,899,749 A | 2/1990 | Laroco |
| 4,912,306 A | 3/1990 | Grise |
| 4,930,317 A | 6/1990 | Klein |
| 4,941,961 A | 7/1990 | Noguchi et al. |
| 4,989,283 A | 2/1991 | Krouskop et al. |
| 5,008,515 A | 4/1991 | McCormack |
| 5,010,233 A | 4/1991 | Henschen |
| 5,023,433 A | 6/1991 | Gordon |
| 5,032,705 A | 7/1991 | Batcheller et al. |
| 5,072,598 A | 12/1991 | Dibrell et al. |
| 5,074,285 A | 12/1991 | Wright |
| 5,086,629 A | 2/1992 | Dibrell et al. |
| 5,255,390 A | 10/1993 | Gross et al. |
| 5,320,164 A | 6/1994 | Szczesuil et al. |
| 5,352,870 A | 10/1994 | Daugherty et al. |
| 5,380,580 A | 1/1995 | Rogers |
| 5,383,918 A | 1/1995 | Panetta et al. |
| 5,395,399 A | 3/1995 | Rosenwald |
| 5,422,462 A | 6/1995 | Kishimoto |
| 5,443,056 A | 8/1995 | Smith |
| 5,473,783 A | 12/1995 | Allen |
| 5,496,358 A | 3/1996 | Rosenwald et al. |
| 5,605,144 A | 2/1997 | Simmons et al. |
| 5,638,438 A | 6/1997 | Keen et al. |
| 5,723,845 A | 3/1998 | Partington |
| 5,755,275 A | 5/1998 | Rose et al. |
| 5,773,275 A | 6/1998 | Anderson |
| 5,815,864 A | 10/1998 | Sloop |
| 5,817,145 A | 10/1998 | Augustine |
| 5,824,996 A | 10/1998 | Kochman |
| 5,835,983 A | 11/1998 | McMahen et al. |
| 5,878,620 A | 3/1999 | Gilbert et al. |
| 5,881,410 A | 3/1999 | Yamada |
| 5,895,973 A | 4/1999 | Fessenden |
| 5,928,274 A | 7/1999 | Augustine |
| 5,932,129 A | 8/1999 | Hyatt |
| 5,948,303 A | 9/1999 | Larson |
| 5,964,792 A | 10/1999 | Augustine |
| 5,970,542 A | 10/1999 | Mays |
| 5,974,605 A | 11/1999 | Dickerhoff |
| 5,986,243 A | 11/1999 | Campf |
| 6,030,412 A | 2/2000 | Klatz et al. |
| 6,038,722 A | 3/2000 | Giori et al. |
| 6,053,910 A | 4/2000 | Fleenor |
| 6,078,026 A | 6/2000 | West |
| 6,084,217 A | 7/2000 | Bulgajewski |
| 6,093,910 A | 7/2000 | McClintock |
| 6,147,333 A | 11/2000 | Mattson |
| 6,149,674 A | 11/2000 | Borders |
| 6,172,344 B1 | 1/2001 | Gordon |
| 6,180,929 B1 | 1/2001 | Pearce |

(56) References Cited

U.S. PATENT DOCUMENTS

| | | |
|---|---|---|
| 6,184,496 B1 | 2/2001 | Pearce |
| 6,189,487 B1 | 2/2001 | Owen |
| 6,210,427 B1 | 4/2001 | Augustine |
| 6,214,000 B1 | 4/2001 | Fleenor |
| 6,215,111 B1 | 4/2001 | Rock |
| 6,229,123 B1 | 5/2001 | Kochman |
| 6,229,126 B1 | 5/2001 | Ulrich et al. |
| 6,235,049 B1 | 5/2001 | Nazerian |
| 6,240,623 B1 | 6/2001 | Johansson |
| 6,348,678 B1 | 2/2002 | Loyd, Sr. et al. |
| 6,373,034 B1 | 4/2002 | Rock |
| 6,403,935 B2 | 6/2002 | Kochman |
| 6,416,534 B1 | 7/2002 | Montagnino et al. |
| 6,434,328 B2 | 8/2002 | Rutherford |
| 6,452,138 B1 | 9/2002 | Kochman |
| 6,452,139 B1 | 9/2002 | Benoit et al. |
| 6,483,087 B2 | 11/2002 | Gardner |
| 6,493,889 B2 | 12/2002 | Kocurek |
| 6,544,258 B2 | 4/2003 | Fleenor et al. |
| 6,565,593 B2 | 5/2003 | Diana |
| 6,582,456 B1 | 6/2003 | Hand |
| 6,705,388 B1 | 3/2004 | Sorgo |
| 6,713,733 B2* | 3/2004 | Kochman ............... H05B 3/342 219/494 |
| 6,723,115 B1 | 4/2004 | Daly |
| 6,730,115 B1 | 5/2004 | Heaton |
| 6,755,852 B2 | 6/2004 | Lachenbruch et al. |
| 6,770,848 B2 | 8/2004 | Haas |
| 6,770,854 B1 | 8/2004 | Keane |
| 6,839,922 B1 | 1/2005 | Foggett |
| 6,872,758 B2 | 3/2005 | Simpson |
| 6,924,467 B2 | 8/2005 | Ellis |
| 6,933,469 B2 | 8/2005 | Ellis |
| 6,967,309 B2 | 11/2005 | Wyatt |
| 6,974,935 B2 | 12/2005 | O'Grady |
| 7,013,509 B2 | 3/2006 | Hickman |
| 7,020,912 B2 | 4/2006 | Berge |
| 7,022,950 B2 | 4/2006 | Haas |
| 7,049,559 B2 | 5/2006 | Ishii et al. |
| 7,053,344 B1 | 5/2006 | Surjan |
| 7,107,629 B2 | 9/2006 | Miros et al. |
| 7,161,120 B1 | 1/2007 | Stroud |
| 7,176,419 B2 | 2/2007 | Ellis |
| 7,181,790 B2 | 2/2007 | Wirtz et al. |
| 7,228,578 B2 | 6/2007 | Linnane |
| 7,268,320 B2 | 9/2007 | Rock et al. |
| 7,282,676 B1 | 10/2007 | Bouchier et al. |
| 7,375,308 B2* | 5/2008 | Ferguson ............ A01M 1/2077 219/528 |
| 7,543,344 B2 | 6/2009 | Augustine |
| 7,714,255 B2 | 5/2010 | Augustine |
| 7,851,729 B2 | 12/2010 | Augustine |
| 8,062,343 B2 | 11/2011 | Augustine et al. |
| 8,065,763 B2 | 11/2011 | Brykalski |
| 8,170,685 B2 | 5/2012 | Docherty et al. |
| 8,283,602 B2 | 10/2012 | Augustine |
| 8,288,693 B2 | 10/2012 | Weiss |
| 8,291,612 B2 | 10/2012 | Ferguson |
| 8,418,297 B2 | 4/2013 | Mikkelsen |
| 8,624,164 B2 | 1/2014 | Deibel |
| 8,698,044 B2 | 4/2014 | Burr |
| 8,772,676 B2* | 7/2014 | Augustine ............... H05B 3/342 219/211 |
| 8,876,812 B2 | 11/2014 | Aramayo |
| 2001/0020303 A1 | 9/2001 | Endo |
| 2002/0005398 A1 | 1/2002 | Gillner |
| 2002/0047007 A1 | 4/2002 | Loyd, Sr. et al. |
| 2002/0073489 A1 | 6/2002 | Rattan et al. |
| 2002/0117495 A1 | 8/2002 | Kochman |
| 2002/0124312 A1 | 9/2002 | Yoon |
| 2003/0023292 A1 | 1/2003 | Gammons et al. |
| 2003/0069621 A1 | 4/2003 | Kushnir |
| 2003/0192121 A1 | 10/2003 | Fleming et al. |
| 2003/0195596 A1 | 10/2003 | Augustine et al. |
| 2003/0208848 A1 | 11/2003 | Flick et al. |
| 2004/0149711 A1 | 8/2004 | Wyatt |
| 2004/0164499 A1 | 8/2004 | Murakami |
| 2004/0174056 A1 | 9/2004 | Gryp et al. |
| 2004/0193237 A1 | 9/2004 | Krueger |
| 2004/0237206 A1 | 12/2004 | Webster |
| 2005/0016982 A1 | 1/2005 | Campf |
| 2005/0051537 A1 | 3/2005 | Lewis |
| 2005/0061122 A1 | 3/2005 | Behringer |
| 2005/0061681 A1 | 3/2005 | Lim et al. |
| 2005/0103353 A1 | 5/2005 | Grahn et al. |
| 2006/0085919 A1 | 4/2006 | Kramer et al. |
| 2006/0120054 A1 | 6/2006 | Buschke |
| 2006/0142828 A1 | 6/2006 | Schorr et al. |
| 2006/0191675 A1 | 8/2006 | Fletcher et al. |
| 2006/0247745 A1 | 11/2006 | Thompson |
| 2006/0260060 A1 | 11/2006 | Apperson |
| 2006/0261055 A1 | 11/2006 | Child et al. |
| 2007/0012675 A1 | 1/2007 | Devroy |
| 2007/0049997 A1 | 3/2007 | Fields et al. |
| 2007/0068916 A1 | 3/2007 | Augustine et al. |
| 2007/0068928 A1* | 3/2007 | Augustine ............... A61F 7/007 219/528 |
| 2007/0068929 A1 | 3/2007 | Augustine et al. |
| 2007/0068930 A1 | 3/2007 | Augustine |
| 2007/0068931 A1 | 3/2007 | Augustine et al. |
| 2007/0068932 A1* | 3/2007 | Hewes ............... A61F 7/007 219/552 |
| 2007/0080155 A1 | 4/2007 | Augustine et al. |
| 2007/0093883 A1 | 4/2007 | Anderson et al. |
| 2007/0101996 A1 | 5/2007 | Carstens |
| 2007/0106353 A1 | 5/2007 | Carstens |
| 2007/0106355 A1 | 5/2007 | Carstens |
| 2007/0108190 A1 | 5/2007 | Ferguson |
| 2007/0152479 A1 | 7/2007 | Howman |
| 2007/0164010 A1 | 7/2007 | Rock |
| 2007/0272673 A1 | 11/2007 | Keane |
| 2007/0284356 A1 | 12/2007 | Findlay |
| 2008/0021530 A1 | 1/2008 | Castellani et al. |
| 2008/0127414 A1 | 6/2008 | Allen |
| 2008/0173629 A1 | 7/2008 | Deibel |
| 2008/0203080 A1 | 8/2008 | Fung |
| 2008/0217587 A1 | 9/2008 | Gaudiana et al. |
| 2008/0249521 A1 | 10/2008 | Dunning et al. |
| 2008/0249524 A1 | 10/2008 | Dunning |
| 2008/0255641 A1 | 10/2008 | Ellis |
| 2008/0281310 A1 | 11/2008 | Dunning et al. |
| 2008/0281311 A1 | 11/2008 | Dunning et al. |
| 2008/0283513 A1 | 11/2008 | Ferguson |
| 2009/0036884 A1 | 2/2009 | Gregg et al. |
| 2009/0078690 A1 | 3/2009 | Lee |
| 2009/0095735 A1 | 4/2009 | Resheff |
| 2009/0099631 A1 | 4/2009 | Augustine et al. |
| 2009/0163984 A1 | 6/2009 | Robinson et al. |
| 2009/0198230 A1 | 8/2009 | Behnke et al. |
| 2009/0222996 A1 | 9/2009 | Balonick |
| 2010/0078807 A1 | 4/2010 | Schulz |
| 2010/0089896 A1 | 4/2010 | Bart |
| 2010/0119704 A1 | 5/2010 | Hemmelgarn |
| 2010/0161016 A1* | 6/2010 | Augustine ............ A61F 7/0097 607/112 |
| 2010/0168825 A1 | 7/2010 | Barbknecht |
| 2010/0200558 A1 | 8/2010 | Liu et al. |
| 2010/0204763 A1 | 8/2010 | Augustine |
| 2010/0222457 A1 | 9/2010 | Wanner |
| 2010/0224612 A1 | 9/2010 | Asami |
| 2010/0279086 A1 | 11/2010 | Park et al. |
| 2010/0283295 A1 | 11/2010 | Smith |
| 2010/0325796 A1 | 12/2010 | Lachenbruch |
| 2011/0031230 A1 | 2/2011 | Kim |
| 2011/0092930 A1 | 4/2011 | Poorman |
| 2011/0099900 A1 | 5/2011 | Weder |
| 2011/0233185 A1 | 9/2011 | Augustine et al. |
| 2012/0065716 A1 | 3/2012 | Gill et al. |
| 2012/0111846 A1 | 5/2012 | Hammerschmidt |
| 2012/0140375 A1 | 6/2012 | Kim et al. |
| 2012/0222192 A1 | 9/2012 | Carey et al. |
| 2012/0238842 A1 | 9/2012 | Colvin, Jr. et al. |
| 2012/0238901 A1 | 9/2012 | Augustine |
| 2012/0273475 A1 | 11/2012 | An |

(56) References Cited

U.S. PATENT DOCUMENTS

| | | | |
|---|---|---|---|
| 2012/0279953 A1 | 11/2012 | Augustine | |
| 2014/0074086 A1 | 3/2014 | MacIntyre-Ellis | |
| 2014/0263265 A1 | 9/2014 | Augustine et al. | |
| 2014/0312027 A1 | 10/2014 | Augustine | |
| 2014/0316494 A1 | 10/2014 | Augustine | |
| 2014/0316495 A1 | 10/2014 | Augustine | |
| 2015/0148874 A1 | 5/2015 | Augustine et al. | |
| 2015/0216610 A1 | 8/2015 | Augustine | |
| 2015/0289817 A1 | 10/2015 | Augustine et al. | |
| 2015/0290027 A1 | 10/2015 | Augustine et al. | |
| 2015/0290062 A1 | 10/2015 | Augustine et al. | |
| 2015/0290065 A1 | 10/2015 | Augustine | |
| 2015/0327332 A1 | 11/2015 | Augustine et al. | |
| 2015/0366367 A1 | 12/2015 | Augustine et al. | |
| 2016/0143091 A1 | 5/2016 | Augustine et al. | |

FOREIGN PATENT DOCUMENTS

| | | |
|---|---|---|
| EP | 787476 A2 | 8/1997 |
| EP | 1374822 A1 | 1/2004 |
| EP | 2662063 A1 | 11/2013 |
| GB | 586745 A | 3/1947 |
| GB | 969253 A | 9/1964 |
| WO | 9925155 A1 | 5/1999 |
| WO | 1999023992 A1 | 5/1999 |
| WO | 0135878 A2 | 5/2001 |
| WO | 2001095841 A1 | 7/2002 |
| WO | 2004093758 A1 | 11/2004 |
| WO | 2007041389 A1 | 4/2007 |
| WO | 2008089412 A1 | 7/2008 |
| WO | 2010107724 A1 | 9/2010 |
| WO | 2012125916 A2 | 9/2012 |
| WO | 2013134477 A1 | 9/2013 |
| WO | 2015147684 A1 | 10/2015 |
| WO | 2015157674 A2 | 10/2015 |

OTHER PUBLICATIONS

International Search Report and the Written Opinion of the International Searching Authority, or the Declaration for International Pat. App. No. PCT/US2015/025392, Jul. 16, 2015, 13 pages, European Patent Office, Rijswijk, The Netherlands.

EeonTex Conductive Testiles, Product Details, www.eeonyx.com/prodte.html, Sep. 19, 2006, pp. 1-5.

Invitation to Pay Additional Fees and, Where Applicable, Protest Fee for International Pat. App. No. PCT/US2015/025374, Jul. 20, 2015, 5 pages, European Patent Office, Rijswijk, The Netherland&.

Invitation to Pay Additional Fees and, Where Applicable, Protest Fee for International Pat. App. No. PCT/US2015/025392, Jul. 16, 2015, 13 pages, European Patent Office, Rijswijk, The Netherlands.

Moritz and Henriques, "Studies of Thermal Injury: The Relative Importance of Time and Surface Temperature in the Causation of Cutaneous Burns", Am. J. Pathology 23:6, Am. J. Pathology 23:695-720, 1947.

Stoll & Greene, "Relati"Relationship Between Pain and Tissue Damage Due to Thermal Radiation, J. Applied Physiolo, J. Applied Physiology 14 (3):373-382, 1959.

Supplementary European Search Report for EP Pat. App. No. 12757173, dated May 22, 2015, 9 pages, European Patent Office, Munich, Germany.

International Patent Application No. PCT/US2015/060659, International Search Report and Written Opinion dated Feb. 5, 2016, 12 pages.

Bair Hugger brochure, retrieved from http://www.bairhugger.com/arizanthealthcare/pdf/600755A.pdf, 2003, 6 pages.

Lenhardt et al., "Local warming and insertion of peripheral venous cannulas: single blinded prospective randomised controlled trial and single blinded randomised crossover trial," British Medical Journal 325:409, Aug. 2002, 4 pages.

* cited by examiner

ELECTRIC HEATING PAD

This application is a continuation-in-part of U.S. application Ser. No. 14/287,292, filed May 27, 2014, which is a continuation of U.S. application Ser. No. 13/460,368, filed Apr. 30, 2012, now U.S. Pat. No. 8,772,676 issued Jul. 8, 2014, which is a continuation of U.S. application Ser. No. 12/050,806, filed Mar. 18, 2008, now U.S. Pat. No. 8,283,602 issued Oct. 9, 2012, which claims priority to U.S. Provisional Patent Application No. 60/895,736, filed Mar. 19, 2007. This application is also a continuation-in-part of three pending U.S. applications including: U.S. Provisional Patent Application No. 62/079,076, filed Nov. 13, 2014; U.S. application Ser. No. 13/422,279, filed Mar. 16, 2012; and U.S. application Ser. No. 14/683,915, filed Apr. 10, 2015. The entire contents of all of these applications are incorporated herein by reference.

TECHNICAL FIELD

The present invention is related to heater assemblies including heating or warming blankets or pads, and more particularly to those including electrical heating elements.

BACKGROUND

It is well established that surgical patients under anesthesia become poikilothermic. This means that the patients lose their ability to control their body temperature and will take on or lose heat depending on the temperature of the environment. Since modern operating rooms are all air conditioned to a relatively low temperature for surgeon comfort, the majority of patients undergoing general anesthesia will lose heat and become clinically hypothermic if not warmed.

There have been many attempts at making heated blankets and pads, including pads in the form of heated underbody supports, heated mattresses and heated mattress overlays for therapeutic patient warming. Therapeutic patient warming is especially important for patients during surgery. It is well known that without therapeutic intra-operative warming, most anesthetized surgical patients will become clinically hypothermic during surgery. Hypothermia has been linked to increased wound infections, increased blood loss, increased cardiac morbidity, prolonged ICU time, prolonged hospital stays, increased cost of surgery and increased death rates.

Over the past 15 years, forced-air warming (FAW) has become one of the "standard of care" for preventing and treating the hypothermia caused by anesthesia and surgery. FAW consists of a large heater/blower attached by a hose to an inflatable air blanket. The warm air is distributed over the patient within the chambers of the blanket and then is exhausted onto the patient through holes in the bottom surface of the blanket.

Although FAW is clinically effective, it suffers from several problems including: a relatively high price; air blowing in the operating room, which can be noisy and can potentially contaminate the surgical field; and bulkiness, which, at times, may obscure the view of the surgeon. Moreover, the low specific heat of air and the rapid loss of heat from air require that the temperature of the air, as it leaves the hose, be dangerously high—in some products as high as 45° C. This poses significant dangers for the patient. Second and third degree burns have occurred both because of contact between the hose and the patient's skin, and by blowing hot air directly from the hose onto the skin without connecting a blanket to the hose. This condition is common enough to have its own name—"hosing." The manufacturers of forced air warming equipment actively warn their users against hosing and the risks it poses to the patient.

To overcome the aforementioned problems with FAW, several companies have developed electric warming blankets. Some of these warming blankets employ flexible heaters, the flexibility of which is desirable to maintain when employing the blankets. In many cases, an electric warming blanket employs a shell for holding the heater and for serving other purposes. For example, in some cases the shell includes layers formed of a substantially water impermeable material to help prevent fluid damage to the heater. Also, when these heaters are used for patient or other care, especially in the operating room, the shell can protect the patient and others in the vicinity from electric shock hazards. In addition to often providing a seal around the heater, the shell often contains a fastening mechanism that must reliably attach the heater to the shell to prevent electrical shorting across the heater during folding of the electric warming blanket.

Because the seals of the shell must be very reliable, the seals have traditionally been adhesive seals that are reinforced with combinations of sewing, rivets, and grommets. Sewing stitches, rivets, and grommets all share one characteristic—they all perforate the material layers to create a mechanical linkage between the layers.

While such a reinforced bond may be desirable for strength, it can create additional problems when used during surgery or medical procedures. For example, heated blankets placed over a patient during a surgery or medical procedure are frequently soiled with waste blood or other body fluids. The fluid waste can saturate the stitching and then dry and accumulate in the thread or the stitch holes. If rivets or grommets are used for reinforcement, additional crevasses are introduced that can trap waste fluids. When the outer shell of the blanket is cleaned by hospital personnel, it is nearly impossible to clean the residual contaminating materials out of the holes, crevasses, and/or stitches. Therefore, the stitching holes and thread, the grommets, rivets and snaps can all become sources of microbial contamination because they cannot be thoroughly cleaned and disinfected.

Prior to the 1990's, warm water mattresses were commonly used. The warm water mattresses went out of common use because they were relatively stiff and inflexible. The stiff water mattress negated any pressure relief that the underlaying support mattress may have provided. As a result, the combination of pressure applied to the boney prominences and the heat from the warm water mattress both reduced blood flow and accelerated metabolism, causing accelerated ischemic pressure injuries to the skin ("bed sores"). Additionally, the warmed water recirculating in the warming system was well known to be grossly contaminated with bacteria, which was especially important when a leak occurred. As a result, warm water mattresses are rarely used today.

Historically, electrically heated pads and blankets for the consumer market have been made with resistive wire heaters. Wire-based heaters have been questionably safe in consumer use. However, in the operating room environment with anesthetized patients, hot spots caused by the wires in normal use and the failure mode of broken heater wires resulting in sparking, arcing and fires are totally unacceptable. Therefore, resistive wire-based heaters are not used in the operating room today.

Since the mid 1990's, a number of inventors have tried unsuccessfully to make effective and safe heated mattresses for operating room use, using flexible, sheet-like electric resistance heaters. The sheet-like heaters have been shown to be more effective in warming the patients because of the even heat production and generally do not cause arcing and sparking when they fail.

Some existing devices employ sheet-like heaters using a polymeric fabric that has been baked at high temperature until it becomes carbonized and is thus conductive of electricity. The carbonization process makes the fabric fragile, and therefore, it may be laminated between two layers of plastic film or fiber-reinforced plastic film for stability and strength. The lamination process results in a relatively stiff, although somewhat flexible, non-stretching, non-conforming heater. The metal foil bus bars are attached to the heater material with an "electrically conductive adhesive or bonding composition . . . " and then encapsulated with polyurethane-coated nylon fabric. The result is a stiff and relatively inflexible bus bar.

Clearly, there is a need for conductive fabric heaters for use in therapeutic heated mattresses that are highly flexible, stretchable in at least one direction and durable without needing lamination to stabilize or protect the heater fabric. There is also a need for bus bar construction that does not result in thick, stiff, inflexible areas along the side edges of the heater. Then, maximally effective and safe therapeutic heated mattresses need to be designed using the stretchable, durable fabric heaters.

In addition to patient warming during surgery, and as known to those skilled in the art, modern surgical techniques typically employ radio frequency (RF) cautery to cut and coagulate bleeding encountered in performing surgical procedures. Every electrosurgical generator system may have an active electrode that is applied by the surgeon to the patient at the surgical site to perform surgery and an electrical return path from the patient back to the generator. The active electrode at the point of contact with the patient may be small in size to produce a high current density in order to produce a surgical effect of cutting or coagulating tissue. The return electrode, which carries the same current as the active electrode, may be large enough in effective surface area at the point of communication with the patient such that a low density current flows from the patient to the return electrode. If a relatively high current density is produced at the return electrode, the temperature of the patient's skin and underlying tissue will rise in this area and can result in a patient burn.

Return electrodes have evolved over the years from small 12×7-inch, flat stainless steel plates coated with a conductive gel that were placed under the patient's buttocks, thigh, shoulders, or any location where gravity could ensure adequate contact. The next development was flexible foam-backed electrodes. These flexible electrodes are about the same size as the stainless steel plates and are coated with a conductive polymer. They have an adhesive border so that they remain attached to the patient without the aid of gravity.

Described as early as 1938 and first introduced into the surgical market in 1960, capacitively coupled return electrodes offer an alternative to conductive return electrodes. Unlike conductive electrodes, which involve direct patient contact, a capacitively coupled electrode is placed close to, but not touching, the patient. It is separated from the patient by a dielectric barrier—that is, a layer of insulating material. This allows the electrode to form a capacitor with the patient. A capacitor is an electrical circuit element used to store a charge temporarily. In use, this type of electrode induces a current flow across the electrode-patient capacitor such that electricity is safely returned from the patient to the electrosurgical unit across a dielectric insulator layer, allowing the desired surgical effect at the surgical site.

A capacitively coupled return electrode consists of a single conductive plate, fabric or film that is encased in a dielectric material. The insulating material does not permit the charge to flow through the electrode to the patient. When placed in close proximity to each other, the conductive plate and the patient become capacitively coupled. Their separation is maintained by the electrode's insulating material, which forms a dielectric barrier between them. For example, a large flat sheet of conductive material that covers a portion of the operating table may be the electrode and the dielectric barrier may consist of plastic film, linens, cushions or other materials that may be placed between the patient and the electrode.

When the active electrode is applied at the surgical site, the electrosurgical unit induces an oscillating radio frequency (RF) voltage through the surgical site and between the patient and the return electrode's conductive plate. As this occurs, several events take place simultaneously. First, an electrical charge accumulates and diminishes in cycles, both on the surface of the patient over lapping the return electrode and on the electrode's capacitive plate, in equal and opposing polarities. Second, the dielectric material becomes polarized: an electrical charge will not move through it. Finally, as the electrical charge moves to and from the surface of the patient's skin, there is a loss of energy that produces a minimal amount of heat within the skin (as happens with a conductive return electrode).

If the dielectric is thin, meaning that the patient and the return electrode are close together—for example less than 2 mm—the capacitive coupling is very efficient. If the distance between the patient and the electrode increases, the efficiency of the coupling decreases. Therefore, minimizing the distance between the patient and the electrode may be desirable. The ability of this design to minimize the distance of both the heater and the grounding electrode from the patient may be particularly desirable with small pediatric patients who have minimal surface area contacting the support surface.

There is some concern that an unnoticed, accidental hole in the electrode's dielectric material could provide a conductive contact with the patient over a very small area, causing a large concentration of current to flow in a small area and to burn the patient. In some cases, thick layers of "self-sealing" gel material have been interposed between the electrode and the dielectric material to prevent a conductive pathway from occurring in the event of a hole in the dielectric material. The gel material is heavy and cumbersome.

Capacitive coupling electrodes generally have been mattress overlays, which are inconvenient, involving extra cleaning Additionally, they are usually non-stretching conductive fabric—for example, woven nylon embedded into a heavy, cumbersome gel pad—which reduces the effectiveness of the pressure-reducing mattress of the surgical table. The conductive silver coating on the fabric electrode also diminishes radiolucency to x-rays, causing x-rays that are shot through the mattress to be grainy or distorted.

The location of the capacitive coupling grounding electrode under the patient is in direct competition for space with heated underbody warming pads and mattresses commonly used in surgery. Heated underbody warming pads and mattresses also work optimally when in close contact with the patient's skin. Therefore, both of these safety technologies may not perform optimally when used simultaneously as two separate devices since seemingly only one or the other can be optimally placed adjacent the patient's skin.

Clearly, there is a need for improvement by combining the capacitive coupling electrode with the heated underbody warming system. However, simply combining the two technologies into a single shell could produce a laminated structure that would be less stretchable, less flexible and less accommodating—further preventing the patient from sinking optimally into the support mattress and increasing the risk of pressure ulcers.

Combining the capacitive coupling electrode with the heated underbody warming system in a single layer of stretchable, flexible material that can serve as a heater and grounding electrode simultaneously would prevent the problems resulting from a two-layer laminate structure and would reduce the cost and complexity of manufacturing.

Accordingly, there remains a need for heated blankets, shells and pads for flexible heaters that are readily and thoroughly cleanable. There also remains a need for improvements in electrosurgical grounding for surgery. In particular, there is a need for devices including these features that also offer pressure relief and prevent bed sores.

Various embodiments of the invention described herein solve one or more of the problems discussed above in addition to other problems that will become apparent.

SUMMARY

Certain embodiments of the invention include a heater assembly such as an electric heating blanket or pad including a flexible sheet-like heating element and a shell. The shell covers the heating blanket or pad and includes two sheets of flexible material welded together. In some embodiments the weld couples the sheets together about the edges of the heating element. In some embodiments, the weld couples the sheets about the edges of the sheets. Although the heating blanket or pad is described as having two sheets welded together, as one of ordinary skill in the art would consider, the two sheets could be formed from one sheet folded over on itself to form the two different sheet layers.

In some embodiments, the heated blanket or pad includes a grounding electrode for electrosurgical equipment. These capacitive coupling grounding electrodes are well known in the arts. In some embodiments, the capacitive grounding electrode is the conductive heater material (e.g., heating element) that is simultaneously incorporated into the circuits of both the heater/power supply/controller and the electrosurgical unit. In some embodiments, the simultaneous use of the heating element material for heating and grounding allows both technologies to be positioned optimally close to the patient's skin for the maximum efficiency of each therapy.

In some embodiments the grounding electrode is the heating element or heater assembly. The heating elements of the instant inventions are preferentially made of conductive or semi-conductive fabrics or films. The conductive or semi-conductive properties of the heating element material allow it to double as a grounding electrode. The heating element/grounding electrode may advantageously be made of a semi-conductive polymer such as polypyrrole. It is well known that the electrical properties of polypyrrole make it a suitable material for absorbing radar. Polypyrrole has been used as a radar absorbing material in "stealth" aircraft and watercraft. The microwave frequencies of radar are not unlike the RF frequencies used in electro-surgery. The semi-conductive properties of polypyrrole that lead to preferential absorption of high frequency electro-magnetic waves are in contrast to electrically conductive properties of composites made from powdered or vaporized carbon or metals. Metal powder particles deposited on the surface of a fabric material may conduct electricity, but do not preferentially absorb high frequency EM waves. Thin metal coatings may allow "tunneling" of some of the EM waves through the spaces between the particles, allowing the waves to pass right through the material without being absorbed. If the metallic coating is thick, "tunneling" may be prevented, but then reflection and scattering of the EM waves may result in decreased absorption. Therefore, the silver-coated fabrics that have been used in many past electrosurgical grounding pads are seemingly not preferential RF energy absorbers. A semi-conductive polymer such as polypyrrole is advantageous in that it is a preferential RF energy absorber.

In other embodiments, the grounding electrode is a separate layer of material positioned near and parallel to the heating element. In this case, the grounding electrode may advantageously be made of a semi-conductive polymer such as polypyrrole irrespective of what the material the heating element is made from.

In some embodiments, the grounding electrode is a separate layer of material, and there is no heating element. In these cases, the grounding electrode may advantageously be made of a semi-conductive polymer such as polypyrrole.

In some embodiments, the grounding electrode wire is connected directly to the grounding electrode (heating element) material. This connection has been used previously and works acceptably as long as the grounding electrode is made of highly conductive material such as silver-coated nylon fabric. The very low resistance to flow through the silver-coated fabric allows the grounding wire to be connected to the electrode in any location.

In some embodiments, the grounding electrode wire is connected to one of the heating element bus bars. Connecting the grounding wire to the bus bar is advantageous when the grounding electrode material is a resistive heater material that adds resistance to the circuit. A grounding wire connected to one end of the heater, rather than to a bus bar, would create a situation wherein the electrical resistance to current flow would be significantly greater for current originating at the far end of the heater compared to current originating at the end of the patient closest to the wire connection. This situation would cause more of the current to flow through the parts of the patient closest to the wire connection and possibly create an unsafe condition. In contrast, since the bus bar runs substantially parallel to the long axis of the patient, along an edge of the grounding electrode, the distance from the bus bar to the patient is relatively equal along its length, and the resistance to the current flow caused by the heater material is thus substantially equal along the entire length of the patient that is contacting the grounding electrode, creating a safe condition.

In some embodiments, the output electrical currents of both the heater/power supply/controller and the electrosurgical generator are "floating," meaning that they are not referenced to earth (ground) and have no electrical potential to earth (ground) or to each other. In some embodiments, the output electrical currents of both the heater/power supply/controller and the electrosurgical unit are "isolated," meaning that they have no electrical potential to and are not referenced to earth (ground). In some embodiments, the output electrical current of the heater/power supply/controller is a direct current. In some embodiments, the output electrical current of the heater/power supply/controller is low voltage, meaning equal to or less than 48 volts DC.

In some embodiments, the temperature sensor of the heated blanket or pad (e.g., underbody warming system, or heated underbody support) is located on the heater assembly, so that it senses the temperature of the heater assembly in contact with the patient. The temperature sensor thus also serves as a safety sensor, decreasing power to the heater assembly excess heat buildup under the patient from the electrosurgical grounding. The heater controller will alarm if the heater temperature exceeds a safe temperature for heating the skin whether the heating is due to the effect of the heater assembly or the capacitive grounding.

In some embodiments, one or both sides of the heating element material are coated with a thin layer of flexible, stretchable elastomeric material such as rubber or silicone. Preferably the elastomeric material is stretchable, flexible, self-sealing and protects the individual fibers of the heating element from moisture damage. This coating of elastomeric material interposed between the electrode and the dielectric material layers serves as second, redundant dielectric layer should an inadvertent hole be put into the outer shell. The redundant dielectric layer would prevent direct electrical coupling between the patient and the electrode material that could cause a burn.

In some embodiments, the heater/grounding electrode is encased in a flexible dielectric shell that can be flexed up along the sides of the small pediatric patient to improve both the heat transfer and capacitive coupling effects. Flexing the heater/grounding electrode places more of the surface area in close contact with the patient's skin for optimal performance of both heat transfer and capacitive grounding.

In some embodiments, the conductive or semi-conductive material is polypyrrole. In some embodiments the compressible material includes a foam material and in some embodiments it includes one or more air filled chambers. For example, in some embodiments of the heater assembly may be a blanket or pad that includes a water resistant shell encasing the heater assembly, including an upper shell and a lower shell that are sealed together along their edges to form a bonded edge, with the heater assembly attached to the shell along one or more edges of the heater assembly. In some embodiments, the heated pad (e.g., heated underbody support pad) also includes a water resistant shell encasing the heater assembly, including an upper shell and a lower shell that are sewn together along their edges to form a sewn and bonded edge. In some embodiments, the heating element has a generally planar shape when not under pressure, is adapted to stretch into a 3 dimensional compound curve without wrinkling or folding while maintaining electrical conductivity in response to pressure, and to return to the same generally planar shape when pressure is removed.

Maximal patient warming effectiveness is achieved by maximally accommodating the patient into the mattress. In other words, maximizing the contact area between the patient's skin and the heated surface of the mattress. The heater and foam (compressible material) or air bladders of the mattress may be easily deformable to allow the patient to sink into the mattress. This accommodation maximizes the patients skin surface area in contact with the mattress and heater, which minimizes the pressure applied to any given point. It also maximizes the surface contact area for heat transfer and maximizes blood flow to the skin in contact with the heat for optimal heat transfer. The accommodation of the patient into the mattress may not be hindered by a stiff, non-conforming, non-stretching, hammocking heater. Additionally, the heater should be near the top surface of the mattress, in thermally conductive contact with the patient's skin, not buried beneath thick layers of foam or fibrous insulation.

In some embodiments, the compressible material comprises one or more flexible air filled chambers. In some embodiments, the compressible material is a foam material. The heater assembly may be attached to the top surface of the layer of compressible material. In some embodiments, the heated underbody support includes a water resistant shell encasing the heating element/heater assembly and having an upper shell and a lower shell that are sealed together along their edges to form a bonded edge. In some embodiments, one or more edges of the heater assembly may be sealed into the bonded edge. In some embodiments, the heater assembly is attached to the upper layer of water resistant shell material. In some embodiments, the heater assembly is attached to the shell only along one or more edges of the heater assembly. In some embodiments, the heated underbody support also includes an electrical inlet, wherein the inlet is bonded to the upper shell and the lower shell and passes between them at the bonded edge.

Electrically heated mattresses are compressible and accommodating, thus the patients sink into the mattress and more body surface area is recruited to help support the weight of the patient. If the proper foam materials are chosen, virtually the entire posterior surface of the patient contacts the mattress. However, even with the added contact surface area, these mattresses are incapable of transferring enough heat to maintain patient normothermia, especially in pediatric patients.

Small pediatric patients have another problem with accommodation into the foam. Their light weight prevents them from sinking into the foam mattress. Therefore expecting the depression into the foam caused by the patients weight to form the foam around the patient's body thereby increasing the contact with their side surfaces, is clearly impossible in pediatrics.

There is a need for a surgical patient warming mattress that has a greater heat transfer capacity. Since the contact temperature cannot be increased without causing burns, seemingly the only option to increase heat transfer is to increase the body surface contact area. The increase the body surface contact area also increases the efficiency of the capacitive coupling of the grounding electrode in the mattress. The instant invention effectively increases the body surface contact area by substantially separating the patient support functions of the mattress from the patient warming and electrosurgical grounding functions of the mattress. By separating these two functions, each can be maximized independently. At the same time, both of the functions are still simultaneously maintained, to provide a safe and effective heated support surface for surgery.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized. The term 'blanket', used to describe embodiments of the present invention, may be considered to encompass heating blankets and pads, and vice-versa. Pads may also be referred to as underbody support systems or mattresses. In other words, features of the invention are applicable to both blankets and pads, regardless of whether a feature is described in a particular embodiment with regard to a blanket or a pad (e.g., including mattress overlays and underbody supports).

Figure 1:
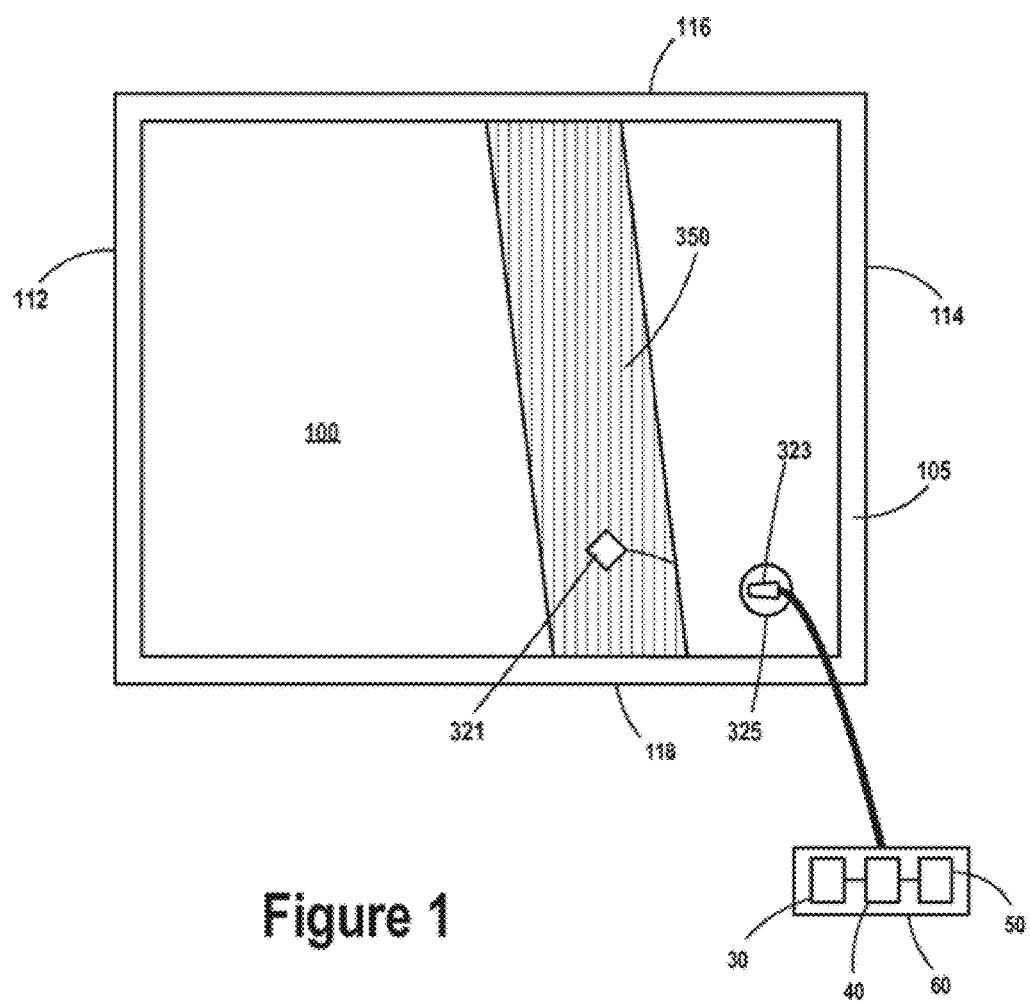
FIG. 1 is a top plan view of a heating blanket or pad, according to some embodiments of the present invention.

FIG. 1 shows a heating blanket or pad 100 according to some embodiments of the present invention. As shown, the heating blanket or pad 100 is generally rectangular. Embodiments of the present invention can be used in connection with a wide variety of heating blankets and pads. For example, in some cases, the heating blanket or pad 100 may be a blanket sized and shaped for the upper body or upper body limb (e.g., a wrap-around blanket), or a blanket sized and shaped for the lower body or lower body limb. In some cases the heating blanket or pad 100 can be used in conjunction with a disposable cover. In other embodiments, the heating blanket or pad 100 may be a mattress overlay or underbody support mattress.

The heating blanket or pad 100 of FIG. 1 includes a shell 105 that can be durable and waterproof. As shown, a portion of the shell 105 is cut away, revealing a heating element assembly 350. The heating element assembly 350 is generally covered by the shell 105 and can extend within the shell 105 between edge 112 and edge 114 and between edge 116 and edge 118. An electrical connector housing 325 and a corresponding connector plug 323 can be coupled to the shell 105, thereby enabling access to a temperature sensor assembly such as those discussed below.

The shell 105 can protect and isolate the heating element assembly 350 from an external environment of heating blanket 100. The shell 105 can include a water-resistant material layer that can form a substantially hermetic seal around the heating element assembly 350. The shell 105 can provide further protection to a patient disposed beneath heating blanket or pad 100 against electrical shock hazards. According to preferred embodiments of the present invention, shell 105 is waterproof to prevent fluids (e.g., bodily fluids, IV fluids, cleaning fluids, etc.) from contacting the heating element assembly 350. In some preferred embodiments, shell 105 may further include an anti-microbial element (e.g., a SILVERion™ antimicrobial fabric available from Domestic Fabrics Corporation or Ultra-Fresh™ from Thomson Research Associates).

According to an illustrative embodiment of the present invention, shell 105 comprises a nylon fabric having an overlay of polyurethane coating to provide waterproofing. The coating can be on at least an inner surface of each of two sheets of the shell, further facilitating a heat seal between the two sheets, according to preferred embodiments. In other embodiments, the shell 105 comprises polyvinyl chloride (PVC) to facilitate an RF weld to bond the sheets. It should be noted that, according to some embodiments of the present invention, a covering for heating element assemblies may be removable and, thus, include a reversible closure facilitating removal of a heating element assembly 350 therefrom and insertion of the same or another heating element assembly 350 therein. In some embodiments, shell 105 comprises a PVC film of sufficient thickness to provide the necessary strength. In some such embodiments, the edge seals can be softer.

In some embodiments, one or more layers may be positioned between the heating element assembly 350 and the shell 105. For example, in some embodiments, [a layer of thermally insulating material] (e.g., polymeric foam or high-loft fibrous non-woven material) can be included in one or more locations. In some instances, a layer of thermally insulating material can be positioned to protect a portion of the patient from the heating element assembly 350 in the event that part of the shell 105 is inadvertently placed under that portion of the patient. In such instances, a layer of thermal insulating material can be positioned between the heating element assembly 350 and the patient-contacting surface of the shell 105. In this way, in the event that part of the shell 105 is inadvertently placed under that portion of the patient, that portion of the patient can contact an insulated portion of the shell 105 rather than a non-insulated portion of the shell 105.

In some instances a layer of thermally insulating material can be positioned to make sure that a maximal amount of heat being generated by the heating element assembly 350 is transferred to the patient. In such instances, a layer of thermally insulating material can help insulate the heating element assembly 350 from the environment and provide a more uniform temperature distribution. The layer of thermally insulating material can be positioned between the heating element assembly 350 and the surface of the shell 105 that does not contact the patient. In this way, a maximal amount of heat being generated by the heating element assembly 350 can be transferred to the patient and not to the surrounding environment.

In some instances a layer of thermally insulating material can be positioned to prevent caregivers from experiencing unwanted contact with activated heating blankets or pads. Other layers (e.g., an electrically insulating layer similar to those discussed elsewhere herein) can be positioned between the heating element assembly 350 and the shell 105.

Figure 2A:
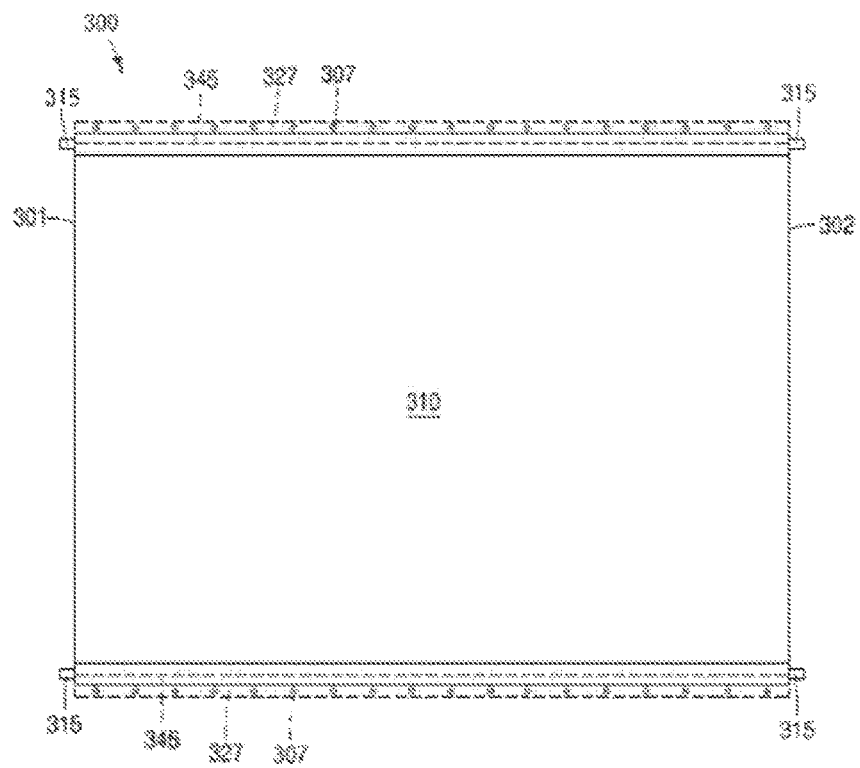
FIG. 2A is a plan view of a flexible heating blanket or pad subassembly for a heating blanket, according to some embodiments of the present invention.
Figure 2B:
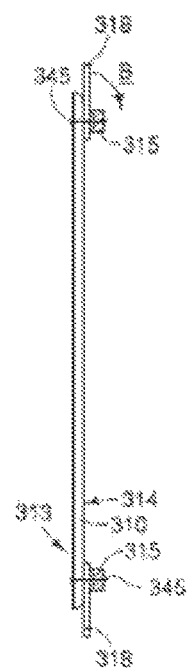
FIG. 2B is an end view of some embodiments of the subassembly shown in FIG. 2A.

FIGS. 2A-2B show an illustrative heating blanket or pad subassembly 300 that can be incorporated into heating element assemblies in some embodiments of the present invention (e.g., heating element assembly 350 of FIG. 1). Referring again to FIGS. 2A-2B, in many embodiments, the heating blanket or pad subassembly 300 is flexible. The heating blanket or pad subassembly 300 can include a flexible sheet-like heating element 310, or heater, which can include a first side edge 301 and a second side edge 302. According to preferred embodiments of the present invention, heating element 310 comprises a conductive fabric or a fabric incorporating closely spaced conductive elements such that heating element 310 has a substantially uniform watt density output, preferably less than approximately 0.5 watts/sq. inch, and more preferably between approximately 0.2 and approximately 0.4 watts/sq. inch, across a surface area, of one or both sides 313, 314 (FIG. 2B).

Some examples of conductive fabrics which may be employed by embodiments of the present invention include, without limitation, carbon fiber fabrics, fabrics made from carbonized fibers, conductive films, or woven or non-woven non-conductive fabric or film substrates coated with a conductive material, for example, polypyrrole, carbonized ink, or metalized ink. In many embodiments, the conductive fabric is a polymeric fabric coated with a conductive polymeric material such as polypyrrole. In addition, the flexible heating element 310 may be made from a matrix of electrically resistant wire or metal traces attached to a fibrous or film material layer.

In some embodiments, in contrast to non-stretchable conductive film heaters, where a carbon (or other conductive material) impregnated plastic film is extruded onto or bonded onto a base layer such as a fabric base layer, the preferred heating element 310 material has a conductive or semi-conductive material coated onto the individual threads or fibers of the carrier fibers prior to weaving or knitting into a fabric. This maintains the natural flexibility and stretchability of the fabric rather than turning the fabric into a non-stretchable fiber reinforced film.

In some embodiments, the conductive or semi-conductive coating comprises a polymer and is bound as a layer surrounding the individual threads or fibers by a process of polymerization. Polymerization results in a very secure bond. The flexible coating on each individual thread or fiber preferably does not crack, fracture or delaminate during flexion. Polymerization of these conductive or semi-conductive materials onto individual fibers of the carrier fabric is a preferable process for producing a durable, flexible and stretchable heater assembly 300. Semi-conductive polymer coatings such as polypyrrole are preferred for this invention, however, other coating processes are anticipated and conductive coatings that use carbon or metal as the conductive material are also anticipated In some embodiments, the conductive material may be stretchable in at least one direction or, alternatively, in at least two directions. One way to create a stretchable fabric heating element (e.g., 310) is to coat a conductive material onto individual threads or fibers of a carrier fabric which may be a non-conductive material. The threads or fibers may be woven or knitted, for example, into a stretchable fabric. Other examples of conductive fabrics which may be employed include, without limitation, carbon fiber fabrics, fabrics made from carbonized fibers, and woven or non-woven substrates coated with a conductive material, for example, polypyrrole, carbonized ink, or metalized ink.

The conductive material may be applied to the fibers or threads before they are woven or knit into a fabric. In this way, the coated threads can move and slide relative to each other as the fabric is stretched, and can return to their original orientation when the stretching is stopped such that the fabric can return to its original shape. Alternatively, the conductive materials that coat the individual fibers in the fabric may be applied after the fabric is woven or knit using a dipping, spraying, coating or polymerization process or combinations thereof. A conductive polymer can be selected that coats to the individual threads without bonding them together such that the threads remain able to slide relative to each other.

The stretchable fabric heating element (e.g., 310) is able to deform in response to a focal pressure applied to the surface of the heater fabric, into a smooth 3-dimensional compound curve without wrinkling or folding. A smooth compound curve cannot be formed out of non-stretchable fabrics or films. The stretchable fabric heating element may also exhibit elastic properties that allow it to revert to its original planar shape when the deforming pressure is relieved. The fabric heating element can be provided with appropriate tensile properties such that the amount of stretch, or strain, required to prevent hammocking and allow accommodation of the patient into the heated mattress or mattress overlay does not result in stresses that exceed the elastic limit of the material. In some embodiments, for example, an increase in the width of a 20 inch wide mattress or mattress overlay of approximately one inch during stretching achieves the desired goals without exceeding the elastic limit of the stretchable fabric heating element or introducing permanent plastic deformation.

FIG. 2A further illustrates subassembly 300 including two bus bars 315 coupled to heating element 310 for powering heating element 310. Each bus bar 315 is shown extending between first and second side edges 301, 302. With reference to FIG. 2B, according to some embodiments, bus bars 315 are coupled to heating element 310 by a stitched coupling 345 (e.g., formed with conductive thread such as silver-coated polyester or nylon thread (Marktek Inc., Chesterfield, Mo.)).

As shown, insulation is provided between the bus bars 315 and the heating element 310. FIG. 2B illustrates subassembly 300 wherein insulating members 318 (e.g., fiberglass material strips having an optional PTFE coating and a thickness of approximately 0.003 inch) extend between bus bars 315 and heating element 310 at each stitched coupling 345, so that electrical contact points between bus bars 315 and heating element 310 are solely defined by the conductive thread of stitched couplings 345. Alternatively, the electrical insulation material layer could be made of polymeric film, a polymeric film reinforced with a fibrous material, a cellulose material, a glass fibrous material, rubber sheeting, polymeric or rubber coated fabric or woven materials or any other suitable electrically insulating material.

Each of the conductive thread stitches of coupling 345 can maintain a stable and constant contact with bus bar 315 on one side and heating element 310 on the other side of insulating member 318. The stitches produce a stable contact in the face of any degree of flexion, so that the potential problem of intermittent contact between bus bar 315 and heating element 310 (that could arise for the embodiment shown in FIG. 2B, where bus bar 315 is in physical contact with heating element 310) can be avoided. The stitches (e.g., 345) are the only electrical connection between bus bar 315 and heating element 310, but, since the conductive thread has a much lower electrical resistance than the conductive fabric of heating element 310, the thread does not heat under normal conditions.

In addition to heating blanket applications described herein, such a design for providing for a uniform and stable conductive interface between a bus bar and a conductive fabric heating element material can be used in other applications. For example, such a design can improve the conductive interface between a bus bar or electrode and a conductive fabric in non-flexible heating elements, in electronic shielding, in radar shielding and other applications of conductive fabrics.

In some preferred embodiments, coupling 345 includes two or more rows of stitches for added security and stability. However, due to the flexible nature of blanket or pad subassembly 300, the thread of stitched couplings 345 may undergo significant stresses. These stresses, over time and with multiple uses of a blanket or pad containing subassembly 300, could lead to one or more fractures along the length of stitched coupling 345. Such a fracture, in other designs, could also result in intermittent contact points, between bus bar 315 and heating element 310 that could lead to a thermal breakdown of heating element 310 along bus bar 315. But, if such a fracture were to occur in the embodiment of FIG. 2B, insulating member 318 may prevent a thermal breakdown of heating element 310, so that only the conductive thread of stitched coupling 345 melts down along bus bar 315. According to some preferred embodiments, more than two rows of stitches are applied to each bus bar 315 for added safety and stability of the bus bar 315/heating element 310 interface.

Alternative threads or yarns employed by embodiments of the present invention may be made of other polymeric or natural fibers coated with other electrically conductive materials. In addition, nickel, gold, platinum and various conductive polymers can be used to make conductive threads. Metal threads such as stainless steel, copper or nickel could also be used for this application.

According to an exemplary embodiment, bus bars 315 are comprised of flattened tubes of braided wires, such as are known to those skilled in the art (e.g., a flat braided silver coated copper wire) and may thus accommodate the thread extending therethrough, passing through openings between the braided wires thereof. In addition such bus bars 315 are flexible to enhance the flexibility of blanket or pad subassembly 300. According to alternate embodiments, bus bars 315 can be a conductive foil or wire, flattened braided wires not formed in tubes, an embroidery of conductive thread, or a printing of conductive ink. Preferably, bus bars 315 are each a flat braided silver-coated copper wire material, since a silver coating has shown superior durability with repeated flexion, as compared to tin-coated wire, for example, and may be less susceptible to oxidative interaction with a polypyrrole coating of heating element 310 according to an embodiment described below. Additionally, an oxidative potential, related to dissimilar metals in contact with one another is reduced if a silver-coated thread is used for stitched coupling 345 of a silver-coated bus bar 315.

According to an exemplary embodiment, a conductive fabric comprising heating element 310 comprises a nonwoven polyester having a basis weight of approximately 170 g/m2 and being 100% coated with polypyrrole (available from Eeonyx Inc., Pinole, Calif.). The coated fabric has an average resistance (e.g., determined with a four point probe measurement) of approximately 15 ohms per square inch. This average resistance is suitable to produce the preferred watt density of 0.2 to 0.4 watts/sq. in. for surface areas of heating element 310 having a width, between bus bars 315, in the neighborhood of about 19 to 28 inches, when powered at about 48 volts. In some embodiments, the basis weight of the non-woven polyester may be chosen in the range of approximately 80-180 g/m2. However, other basis weights may be engineered to operate adequately are therefore within the scope of embodiments of the invention.

A resistance of such a conductive fabric may be tailored for different widths between bus bars 315 (wider requiring a lower resistance and narrower requiring a higher resistance) by increasing or decreasing a surface area of the fabric that can receive the conductive coating. In some instances, this can be achieved by increasing or decreasing the basis weight of the nonwoven. Resistance over the surface area of the conductive fabrics (e.g., 310) is generally uniform in many embodiments of the present invention. However, the resistance over different portions of the surface area of conductive fabrics such as these may vary (e.g., due to (a) variation in a thickness of a conductive coating, (b) variation within the conductive coating itself, (c) variation in effective surface area of the substrate which is available to receive the conductive coating, or (d) variation in the density of the substrate itself). Local surface resistance across a heating element, for example heating element 310, is directly related to heat generation according to the following relationship:

$$Q(\text{Joules}) = I^2(\text{Amps}) \times R(\text{Ohms})$$

Variability in resistance thus translates into variability in heat generation, which can ultimately manifest as a variation in temperature.

According to preferred embodiments of the present invention, which are employed to warm patients undergoing surgery, precise temperature control is desirable. Means for determining heating element 310 temperatures, which average out temperature variability caused by resistance variability across a surface of the heating element 310, are described below in conjunction with FIG. 3A.

Referring again to FIGS. 2A-2B, the flexibility of blanket or pad subassembly 300 can allow blanket or pad subassembly 300 to conform to the contours of a body (e.g., all or a portion of a patient undergoing surgery). This flexibility can be provided primarily by flexible heating element 310 and can be optionally enhanced by the incorporation of flexible bus bars 315. Conforming to the contours of a patient's body is preferable to simply bridging across high spots of the body. Such conformance may optimize a conductive heat transfer from heating element 310 to a surface of the body.

The uniform watt-density output across the surface areas of preferred embodiments of heating element 310 translates into generally uniform heating of the surface areas, but not necessarily a uniform temperature. For example, at locations of heating element 310 which are in conductive contact with a body acting as a heat sink, the heat is efficiently drawn away from heating element 310 and into the body (e.g., by blood flow). At the same time, at those locations where heating element 310 does not come into conductive contact with the patient's body, an insulating air gap exists between the body and those portions, so that the heat is not drawn off those portions as easily. Therefore, those portions of heating element 310 not in conductive contact with the body will gain in temperature, since heat is not transferred as efficiently from these portions as from those in conductive contact with the body. The 'non-contacting' portions will reach a higher equilibrium temperature than that of the 'contacting' portions, when the radiant and convective heat loss equal the constant heat production through heating element 310. Since the heat generation is generally uniform, the heat flux to the patient will also be generally uniform. However, at the non-contacting locations, the temperature is higher to achieve the same flux as the contacting portions.

Some of the extra heat from the higher temperatures at the non-contacting portions can therefore be dissipated out the back of the blanket or pad 100 instead of into the patient.

Although radiant and convective heat transfer are more efficient at higher heater temperatures, the laws of thermodynamics dictate that as long as there is a uniform watt-density of heat production, even at the higher temperature, the radiant and convective heat transfer from a blanket or pad of this construction will result in a generally uniform heat flux from the blanket or pad. Therefore, by controlling the 'contacting' portions to a safe temperature (e.g., via a temperature sensor assembly 321 coupled to heating element 310 in a location where heating element 310 will be in conductive contact with the body), the 'non-contacting' portions, will also be operating at a safe temperature because of the less efficient radiant and convective heat transfer.

According to preferred embodiments, heating element 310 comprises a conductive fabric having a relatively small thermal mass. When a portion of such a heating element that is operating at the higher temperature is touched, suddenly converting a 'non-contacting' portion into a 'contacting' portion, that portion will cool almost instantly to the lower operating temperature.

Figure 3A:
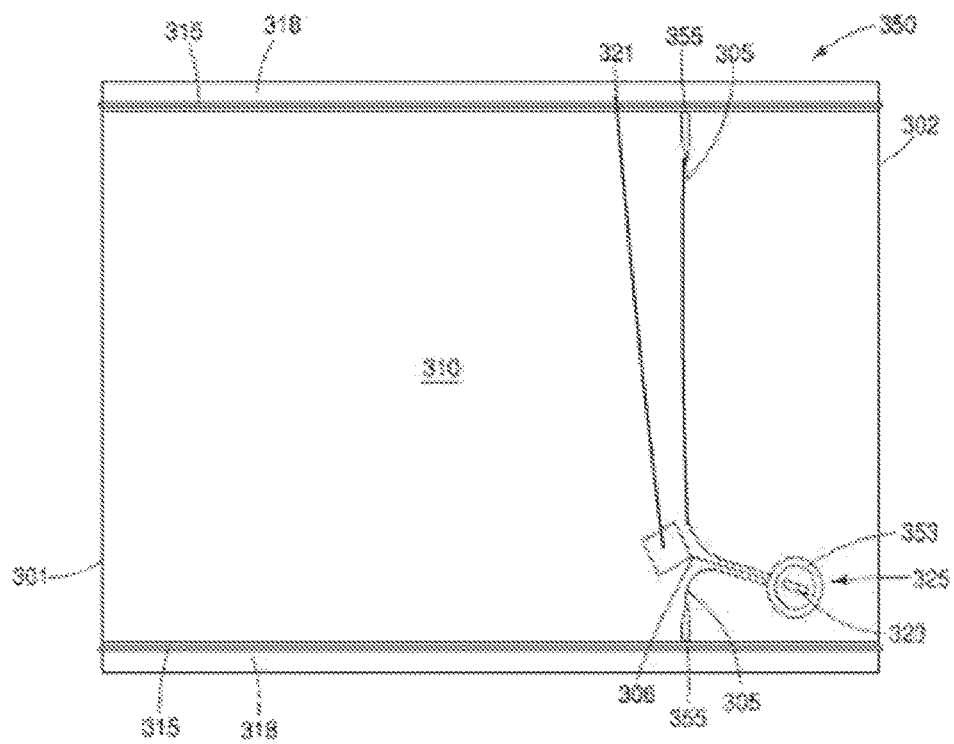
FIG. 3A is a top plan view of a heating element assembly, according to some embodiments of the present invention, which may be incorporated in the blanket or pad shown in FIG. 1.
Figure 3B:
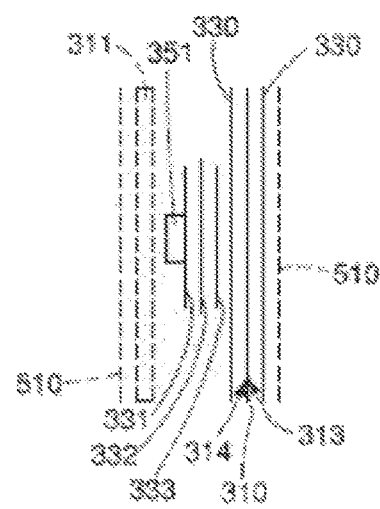
FIG. 3B is a section view of the temperature sensor assembly of FIG. 3A.

FIGS. 3A-3B show a heating element assembly 350 similar to the heating element assembly 350 of FIG. 1. Referring again to FIGS. 3A-3B, the heating element assembly 350 can include a temperature sensor assembly 321. As shown, the temperature sensor assembly 321 is coupled to heating element 310 at a location where heating element 310 would come into conductive contact with the patient. This can assist in maintaining a safe temperature distribution across heating element 310. The more constant the temperature information, the more the temperature controller can rely on it in controlling the heater (e.g., heating element 310, heating element assembly 350) temperature. In some embodiments, the temperature sensor assembly 321 can even be provided separately from the heating blanket or pad.

According to embodiments of the present invention, zones of heating element 310 may be differentiated according to whether or not portions of heating element 310 are in conductive contact with a body (e.g., a patient undergoing surgery). In some embodiments, the threshold temperature is between 37 and 43° C. In one particular embodiment, the threshold temperature is 43° C. A temperature of 43° C. has been shown to provide beneficial warming to a patient without providing excessive heat. In the case of conductive heating, gentle external pressure may be applied to a heating blanket or pad 100 including heating element 310. Such pressure conforms heating element 310 into better conductive contact with the patient to improve heat transfer. However, if excessive pressure is applied, the blood flow to that skin may be reduced at the same time that the heat transfer is improved and this combination of heat and pressure to the skin can be dangerous. It is well known that patients with poor perfusion should not have prolonged contact with temperatures in excess of approximately 42° C. Several studies show 42° C. to be the highest skin temperature that cannot cause thermal damage to normally perfused skin, even with prolonged exposure. (Stoll & Greene, Relationship Between Pain and Tissue Damage Due to Thermal Radiation. J. Applied Physiology 14(3):373-382. 1959; and Moritz and Henriques, Studies of Thermal Injury: The Relative Importance of Time and Surface Temperature in the Causation of Cutaneous Burns. Am. J. Pathology 23:695-720, 1947). Thus, according to certain embodiments of the present invention, the portion of heating element 310 that is in conductive contact with the patient is controlled to approximately 43° C. in order to achieve a temperature of about 41-42° C. on a surface of a heating blanket or pad cover (e.g., shell 105 of FIG. 1) that surrounds heating element 310.

FIG. 3B illustrates the temperature sensor assembly 321 assembled on side 314 of the heating element 310. As shown, the heating element 310 is overlaid on both sides 313, 314 with an electrically insulating layer 330. The electrically insulating layer 330 is preferably formed of a flexible non-woven very low loft fibrous material (e.g., 1.5 ounces-per-square-yard nylon), which is preferably laminated to sides 313, 314 with a hotmelt laminating adhesive. In some embodiments, the adhesive is applied over the entire interfaces between insulating layer 330 and heating element 310. Other examples of suitable materials for insulating layer 330 include, without limitation, polymeric foam, a woven fabric, such as cotton or fiberglass, and a relatively thin plastic film, cotton, and a non-flammable material, such as fiberglass or treated cotton. According to preferred embodiments, overlaid insulating layers 330 prevent electrical shorting of one portion of heating element 310 with another portion of heating element 310 if the heating element 310 is folded over onto itself. Many such embodiments prevent electrical shorting without compromising the flexibility of heating assembly 350. Heating element assembly 350 may be powered by a relatively low voltage (approximately 48V). Insulating layers 330 may even be porous in nature to further maintain the desired flexibility of assembly 350.

As shown in FIG. 3A, an assembly of leads 305, 306 and junctions 355 can connect the bus bars 315 and the temperature sensor assembly 321 to an electrical connector housing 325. Leads 305 couple the connector housing 325 to bus bars 315 at junctions 355. Lead 306 couples the temperature sensor assembly 321 to the connector housing 325. In many embodiments, leads 305, 306 extend over any insulating layer (e.g., 330 in FIG. 3B) and into the electrical connector housing 325. As is noted above (see discussion in connection with FIG. 1) and discussed in greater detail below (see discussion in connection with FIG. 4A), electrical connector housing 325 can contain a connector plug 323.

Returning now to FIG. 3B, the illustrative temperature sensor assembly 321 will be described in greater detail. The temperature sensor assembly 321 can include a temperature sensor 351 (e.g., a surface mount chip thermistor (such as a Panasonic ERT-J1VG103FA: 10K, 1% chip thermistor)) soldered to an etched metal foil. In many embodiments, a substrate 331 (e.g., of polyimide (Kapton)) surrounds the temperature sensor 351. A heat spreader 332 (e.g., a copper or aluminum foil) can be mounted to an opposite side of substrate 331 (e.g., being bonded with a pressure sensitive adhesive). Substrate 331 can be relatively thin (e.g., about 0.0005-inch thick) so that heat transfer between heat spreader 332 and sensor is not significantly impeded.

In some embodiments, the temperature sensor 351 is positioned such that the regions surrounding sensor 351 will be in conductive contact with the body when a heating blanket or pad is placed over a body. As previously described, in many instances, it is desirable that a temperature of approximately 43° C. be maintained over a surface of heating element 310 which is in conductive contact with a body of a patient undergoing surgery. An additional alternate embodiment is contemplated in which an array of temperature sensors are positioned over the surface of heating element 310, being spaced apart to collect temperature readings. In some such embodiments, the collected temperatures can be averaged to account for resistance variance.

Figure 4A:
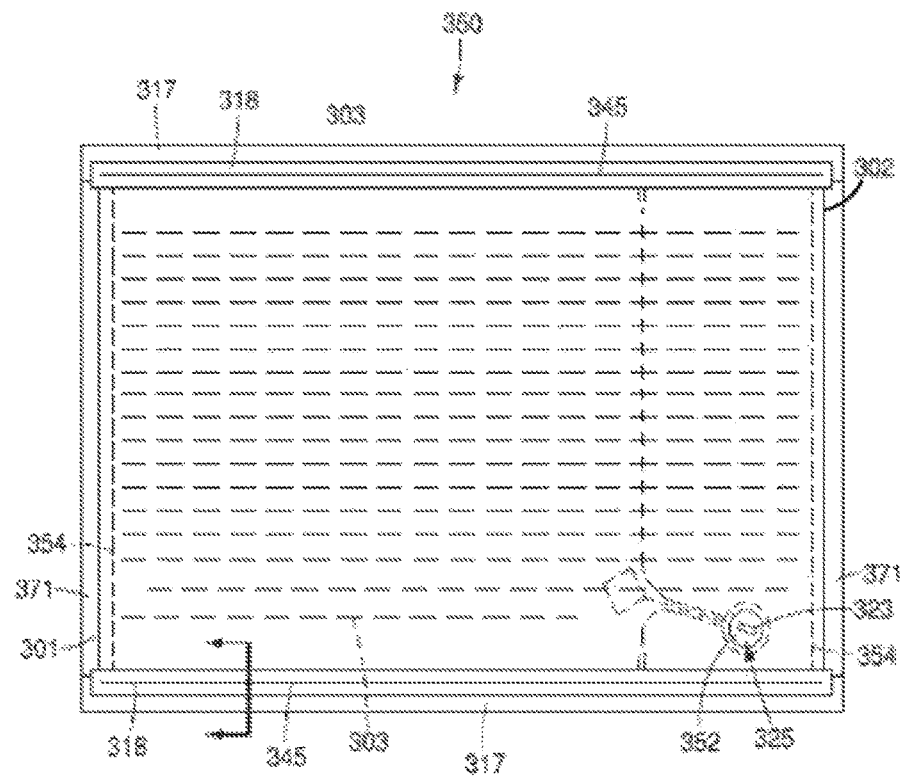
FIG. 4A is a top plan view of a heating element assembly, which may be incorporated in the blanket or pad shown in FIG. 1.
Figure 4B:
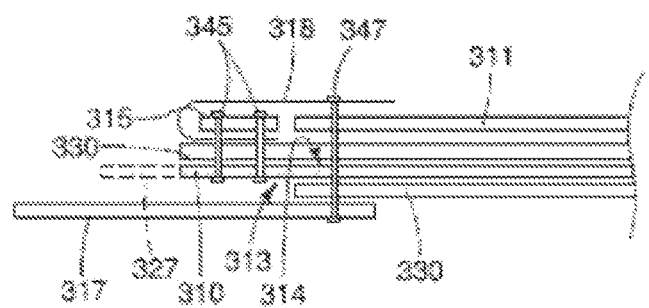
FIG. 4B is a cross-section view through section line 4B-4B of FIG. 4A.

FIGS. 4A-4B show a heating element assembly 350 that may be incorporated into a heating blanket or pad (e.g., heating blanket or pad 100 of FIG. 1). As shown, the heating element assembly 350 includes heating element 310 overlaid with electrical insulation 330 on both sides 313, 314 and a thermal insulation layer 311 extending over the top side 314 thereof (dashed lines show leads and sensor assembly beneath layer 311).

A heating blanket or pad may 100 include a layer of thermal insulation 311 extending over a top side (corresponding to side 314 of heating element 310 as shown in FIG. 2B) of heating assembly 350 as discussed above. According to the illustrated embodiment, layer 311 is inserted beneath a portion of each insulating member 318. The insulating members 318 have been folded over the respective bus bar 315 (e.g., as illustrated by arrow B in FIG. 2B), and then held in place by a respective row of nonconductive stitching 347 that extends through insulating member 318, layer 311 and heating element 310. Although not shown, it should be appreciated that layer 311 may further extend over bus bars 315. Although insulating layer 330 is shown extending beneath layer 311 on side 314 of heating element 310, according to alternate embodiments, layer 311 independently performs as a thermal and electrical insulation so that insulating layer 330 is not required on side 314 of heating element 310. FIG. 4A further illustrates, with longitudinally extending dashed lines, a plurality of optional slits 303 in layer 311, which may extend partially or completely through layer 311, in order to increase the flexibility of assembly 350. Such slits 303 are desirable if a thickness or density of layer 311 is such that it prevents the heating blanket or pad 100 from draping (e.g., curving, deforming) effectively about a patient. The optional slits 303 are preferably formed, for example, extending only partially through layer 311 starting from an upper surface thereof, to allow bending of the heating blanket or pad 100 about a patient and to prevent bending of the heating blanket or pad 100 in the opposition direction.

Returning now to FIG. 3A, to be referenced in conjunction with FIGS. 1 and 4A, connector housing 325 and connector plug 323 will be described in greater detail. According to certain embodiments, housing 325 is an injection molded thermoplastic (e.g., PVC) and may be coupled to assembly 350 by being stitched into place, over insulating layer 330. FIG. 3A shows housing 325 including a flange 353 through which such stitching can extend.

Referring to FIGS. 1 and 4A, in some embodiments, a surface of flange 353 of housing 325 protrudes through a hole formed in thermal insulating layer 311 so that a seal may be formed (e.g., by adhesive bonding and/or welding, such as heat sealing) between an inner surface of shell 105 and surface 352. According to one embodiment, wherein housing 325 is injection molded PVC and the inner surface of shell 105 is likewise PVC, housing 325 is sealed to shell 105 via a solvent bond. It may be appreciated that the location of the connector plug 323 is suitable to keep the corresponding connector cord well away from the surgical field. In embodiments in which the inner surface of shell 105 is coated with polyurethane and the housing 325 is injection molded PVC, an intermediate adhesive can be used to allow for a heat seal connection (e.g., a solvent bond adhesive can be applied to the housing 325, and the polyurethane film can be heat sealed to the exposed adhesive).

FIGS. 4A-4B further illustrate a pair of securing strips 317, each extending laterally from and alongside respective lateral portions of heating element 310, parallel to bus bars 315, and each coupled to side 313 of heating element 310 by the respective row of non-conductive stitching 347. Another pair of securing strips 371 is shown in FIG. 4A, each strip 371 extending longitudinally from and alongside respective side edges 301, 302 of heating element 310 and being coupled thereto by a respective row of non-conductive stitching 354. Strips 371 may extend over layer 311 or beneath heating element 310. As shown, strips 317 preferably extend over conductive stitching of stitched coupling 345 on side 313 of heating element 310. The strips 317 can provide a layer of insulation that can prevent shorting between portions of side 313 of heating element 310 if heating element 310 were to fold over on itself along rows of conductive stitching of stitched coupling 345 that couple bus bars 315 to heating element 310. In some embodiments, strips 317 may alternately extend over insulating member 318 on the opposite side of heating element 310. According to the illustrated embodiment, securing strips 317 and 371 are made of a polymer material (e.g., PVC). They may be heat sealed between the sheets of shell (105 of FIG. 1) in corresponding areas of the heat seal zone in order to secure heating element assembly 350 within a corresponding gap between the two sheets of shell (105 of FIG. 1). According to an alternate embodiment, for example, shown by dashed lines in FIGS. 2A and 4B, heating element 310 extends laterally out from each bus bar 315 to a securing edge 327, which may include one or more slots or holes 307 extending therethrough so that inner surfaces of sheets of shell (105 of FIG. 1) can contact one another to be sealed together and thereby hold edges 327.

Referring to FIG. 1, connector plug 323 can protrude from shell 105 of the heating blanket 100. An extension cable (e.g., FIG. 1) may couple the heating element assembly 350 to a console 60. The console 60 includes a shut-off timer 30 and a power source 50 each coupled to a control system (e.g., controller) 41. The shut-off timer 30 can be operatively coupled to the control system 41, meaning that the shut-off timer 30 can be integrated into the control system 41, the shut-off timer 30 can be a separate component, or the shut-off timer 30 and the control system 41 can have any other suitable functional relationship. The temperature sensor assembly 321 can be configured to provide temperature information to the control system 41, which may act as a temperature controller. The controller may function to interrupt such power supply (e.g., in an over-temperature condition) or to modify the duty cycle to control the heating element temperature.

The power source 50 and power type can be any type known in the art. In certain embodiments, the power source 50 supplies a straight-line DC voltage to the control system 41, and the control system 41 provides a pulse-width-modulated voltage (e.g., at a 75% duty cycle) to the heating element assembly 350. Of course, other duty cycles and/or voltage levels can be used based on the design of the blanket or pad 100 and its heating element in order to achieve a desired threshold temperature in a reasonable amount of time. Too high of voltage or duty cycle, while decreasing the time to reach the desired temperature threshold, may increase the amount of temperature overshoot before the control system 41 reduces or shuts off power. Moreover, in the case of temperature sensor (e.g., 321) failure, thermal runaway presents a greater concern with relatively higher voltage or duty cycle settings. Too low of a voltage or duty cycle may cause unreasonably long warm-up times.

As discussed above, warming blankets and pads in accordance with embodiments of the invention include or make use of a shell or covering, such as shell 105 shown in FIG. 1. Several embodiments of such shells will now be described in greater detail, although it should be understood that these embodiments are for illustrative purposes only.

Figure 5A:
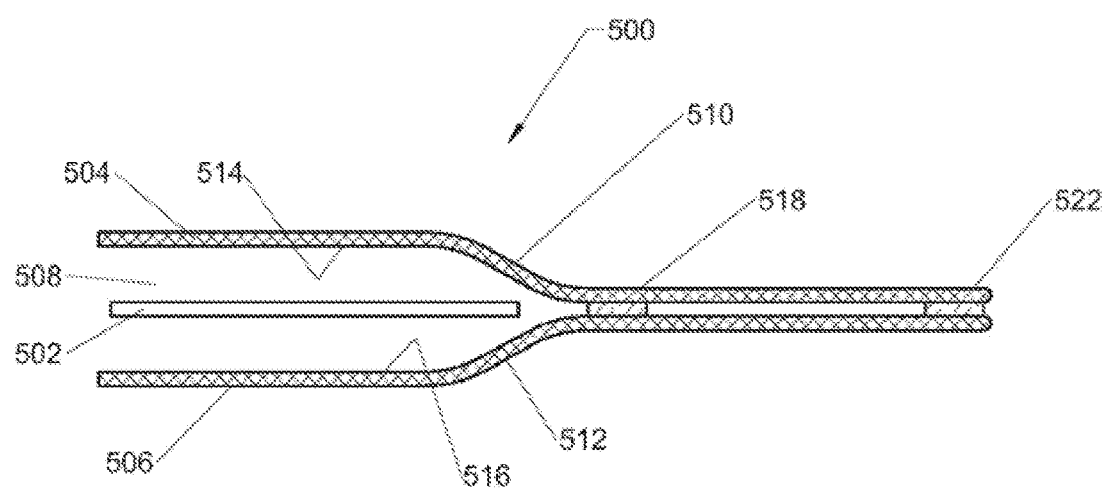
FIG. 5A is a cross-section of a shell containing a heating element according to some embodiments of the present invention.

FIG. 5A is a cross-section of a shell 500 containing a heating element 502 in accordance with some embodiments of the invention. The shell 500 can include a top sheet 504 and a bottom sheet 506 that are welded or coupled at one or more locations in order to define a pocket or pouch 508 that can enclose the heating element 502. Heating element 502 may include characteristics of heating element 310 or may be included in a heating element assembly such as 350. Any type of suitable weld may be used, such as heat welding (heat bonding), RF welding, ultrasonic welding, etc., depending on the type of materials used in sheets 504, 506. Each sheet 504 and 506 can comprise a flexible, substantially water-resistant material and include the ability to be welded together. As one of ordinary skill in the art would consider, sheets 504, 506 may be formed of two or more distinct sheets of material, including a single sheet of material folded over on itself or any other suitable construction. In some embodiments, the water-resistant material includes a single layer, and in some embodiments, the sheets 504, 506 are comprised of a laminate of two or more layers. For instance, in some embodiments one or both of sheets 504, 506 are comprised of a single layer of polyvinyl chloride (PVC). In such embodiments where PVC is used, high frequency or RF welding (RF heat sealing) may be used to bond the sheets 504, 506 together. PVC sheets also provide a water-resistant material in order to protect the heating element 502 from fluids to which the heating blanket or pad 100 is exposed.

In some embodiments, one or both of sheets 504, 506 include respective strengthening layers 510, 512 that provide strength and color to the shell 500. For example, the strengthening layers 510, 512 can be a fibrous material such as woven nylon. It will be appreciated that other materials can also be used for this layer.

With further reference to FIG. 5A, sheets 504, 506 can each also include a second layer 514, 516 located along an inside surface of the sheets 504, 506. These second layers 514, 516 may in some embodiments provide a water-resistant layer in order to protect the heating element 502 from fluids to which the heating blanket or pad is exposed. For example, the second layers 514, 516 may be a polymeric film attached to the strengthening layer. In some embodiments, the second layers 514, 516 are preferably polymeric film layers that are a durable and made of a weldable material, such as urethane or vinyl, which can be laminated or extrusion coated on to the strengthening layers 510, 512 and the second layers 514, 516 may be welded together via heating bonding along the bonding points.

In some embodiments, one or both of sheets 504, 506 include a third layer laminated to their respective outer surfaces. The third layer, in some embodiments, is a polymeric layer, which may or may not be the same material as second layers 514, 516 in some embodiments. For example, the third layer may comprise a polymeric layer that can substantially seal one or both of the strengthening layers so that it cannot be substantially wetted. In some embodiments, the third layer may also be somewhat tacky so that it prevents the blanket from slipping when applied over a patient, or a patient from slipping when provided on a pad. The third layer may also comprise a material with the ability to limit and/or prevent iodine and cleaning solutions from staining the blanket or pad. Examples of materials that could serve this purpose include vinyl and silicone.

With further reference to FIG. 5A, top sheet 504 (e.g., first sheet) and bottom sheet 506 (e.g., bottom sheet) can be positioned on opposing sides of heating element 502 to envelope the heating element. Although descriptive terms "top" and "bottom" are used herein, it will be appreciated that in some embodiments, the sheets 504 and 506 may be identical and that either sheet may be referred to as "top" or "bottom", or "first" and second. Sheets 504 and 506 may be formed of a singular piece of material folded over on itself to provide the two sheets, or at least two sheets. Although sometimes referred to as a first sheet 504 and second sheet 506, the first and second sheets 504, 506 may be formed of a singular piece of material folded over on itself to provide the first sheet 504 and the second sheet 506. As shown in the embodiment of FIG. 5A, the sheets 504, 506 are positioned so that the weldable layers 514, 516 of each sheet oppose each other.

Figure 5B:
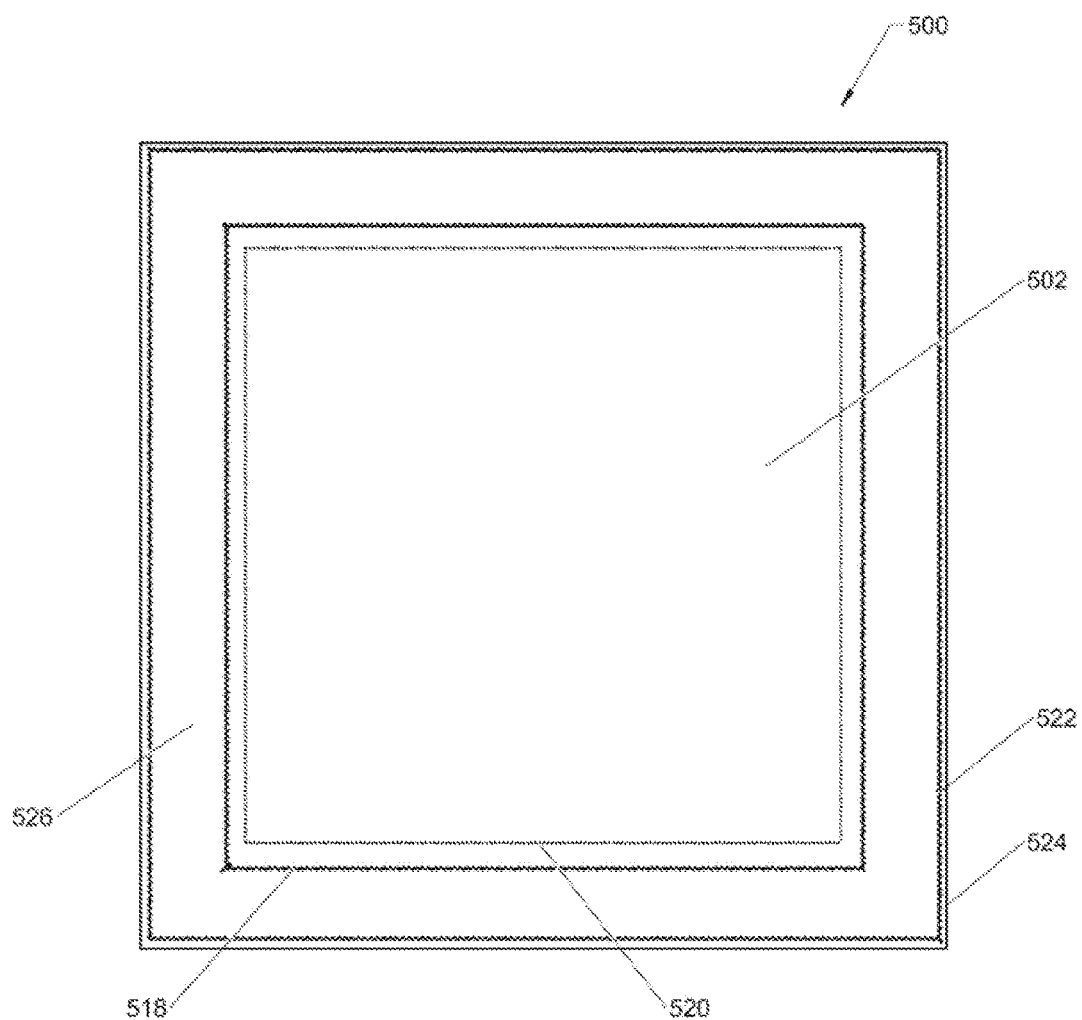
FIG. 5B is a top plan view of the shell of FIG. 5A.

FIG. 5B is a top plan view of the heating blanket or pad 500 depicted in FIG. 5A. In some embodiments, the sheets 504, 506 are sized to completely cover the heating element 502, and can extend beyond all edges (e.g., top, bottom, right and left side edges in FIG. 5B) of the heating element 502. In some embodiments, the heating element 502 is substantially hermetically sealed into the shell 500 formed by the two sheets 504, 506 (e.g., two or more distinct sheets or one sheet folded over on itself to form two sheets). As shown in the embodiment of FIGS. 5A and 5B, the sheets 504, 506 are coupled together along two welds. A first weld 518 can extend about a perimeter 520 of the heating element 502, thus surrounding the entire periphery of the heating element 502. A second weld 522 can extend about a perimeter edge 524 of the sheets 504, 506, thus sealing the periphery of the sheets 504, 506 together. In some embodiments, a space 526 between the first weld 518 and the second weld 522 may be totally or partially welded together. In alternate embodiments, the space 526 between the welds 518, 520 may contain other structural components of the blanket or pad as previously described and further discussed below. For example, the space 526 can enclose weighting members, the added weight of which helps retain the blanket or pad in position and against the patient.

The weld(s) used in some embodiments to create a substantially hermetically sealed shell (e.g., 105; 504, 506) for protecting the heating element (e.g., 310, 502) provides a number of advantages over traditional bonding mechanisms such as sewing, stitches, rivets or grommets that create or reinforce a seal. In certain embodiments of those that employ a heat sealed shell, the external surface of the substantially hermetically sealed shell is not punctured by needle holes, sewing, stitching, rivets, grommets or other fasteners. These traditional fasteners create holes and can accumulate contaminants from blood and body fluids. These holes, crevasses, and fibrous materials such as thread are difficult or even impossible to clean with standard cleaning methods and solutions. Exemplary heating blankets and pads described herein can advantageously have a smooth, non-violated shell, without external attachments or physical places to trap contaminants, thus providing a readily and thoroughly cleanable heating blanket or pad in some embodiments. As will be appreciated, the welded construction used in some embodiments can also facilitate a variety of features that would otherwise require traditional fasteners such as sewing, stitching, riveting, grommets or snaps.

Figure 6:
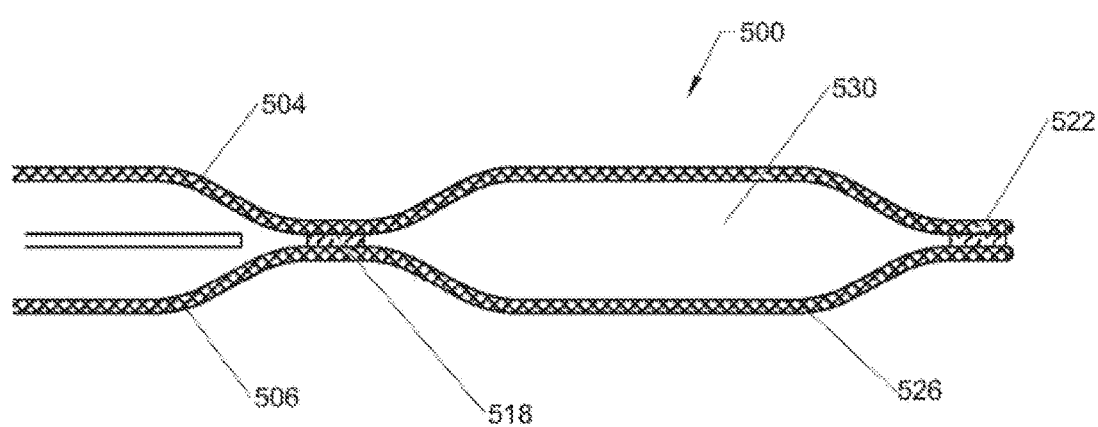
FIG. 6 is a cross-section of a shell containing an air pocket according to some embodiments of the present invention.

In some embodiments, portions of the shell extending beyond the perimeter of the heating element can form non-heated edge flaps of the heating blanket or pad, such as those described above. Exemplary non-heated edge flaps can preferably extend from 1 inch to 24 inches away from the perimeter of the heating element, although it will be appreciated that any suitable length of extension is possible. The non-heated edge flaps can be used to create a cocoon-like space that traps the heat from the heater in a space around the patient. For example, in alternative embodiments, the edges 112, 114, 116, and 118 of the heating blanket or pad 100 depicted in FIG. 1 can include non-heated edge flaps instead of lateral portions of the heating element 310. The non-heated edge flaps can thus create a thermal barrier between the heater edge and the operating table or bed. In some embodiments, the two sheets of the non-heated edge flaps may be partially or completely welded together between the first weld about the perimeter of the heating element and the second weld about the perimeter of the warming blanket or pad. With reference to FIG. 6, in embodiments with a partial weld, the non-welded area may include an air pocket 530. Air can be introduced into the space 526 between the first weld 518 and the second weld 522. Embodiments with such an air pocket 530 can thus provide a thermal barrier that further limits the escape of heat from the space around the patient.

Figure 7A:
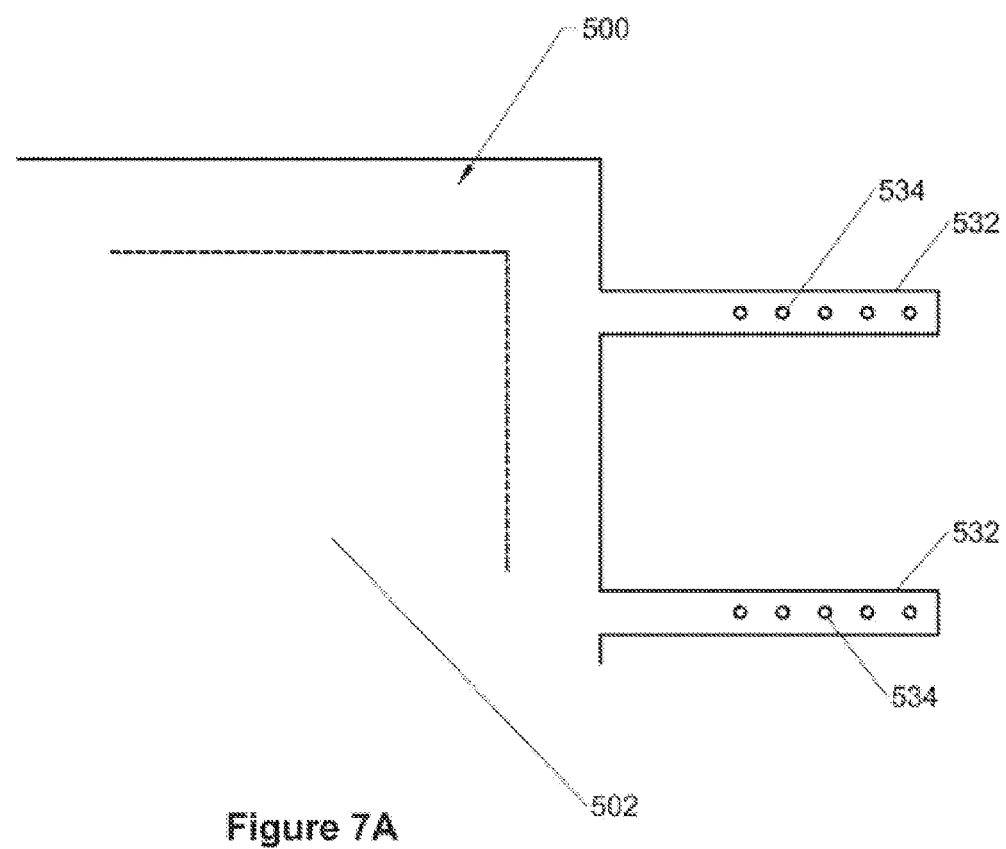
FIG. 7A is a top plan view of a shell having straps according to some embodiments of the present invention.
Figure 7B:
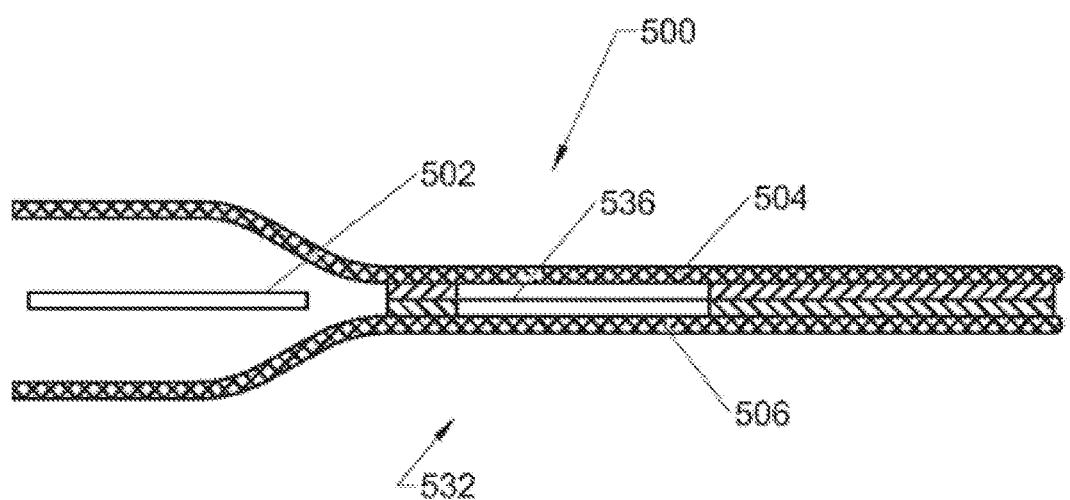
FIG. 7B is a cross-section of the shell of FIG. 7A.

With reference to FIG. 7A, some exemplary heating blankets and pads can include one or more straps 532 extending from the blanket or pad for securing the blanket in place over the patient or the pad in place under the patient. In some embodiments, the straps 532 are preferably of the same material and contiguous with the sheets 504, 506 making up the shell 500 and protrude from the edges of the sheets 504, 506 such that there is no seam joining the straps 532 with the sheets 504, 506. In some embodiments, holes 534 can be punched in the straps 532 to facilitate buckling the straps (e.g., to another blanket strap extending from a different edge of the blanket, to a protuberance extending from the blanket, etc.), hanging the warming blanket, or other common uses. With reference to FIG. 7B, some embodiments can include a reinforcing layer 536 positioned between the sheets 504, 506 before they are welded in order to reinforce the straps 532. For example, the reinforcing layer 536 can in some embodiments comprise a plastic film such as a urethane film. The reinforcing layer 536 may be formed in addition to strengthening layer of sheets 504, 506 described above. Alternatively, the reinforcing layer 536 could be formed by the inclusion of the strengthening layer 510, 512 on one or both of sheets 504, 506 at the strap locations shown in FIG. 7A. As will be appreciated, the straps 532 are provided with the warming blanket or pad without the addition of sewing, stitching, grommets or other traditional fasteners, thus providing the advantages previously discussed.

Figure 8:
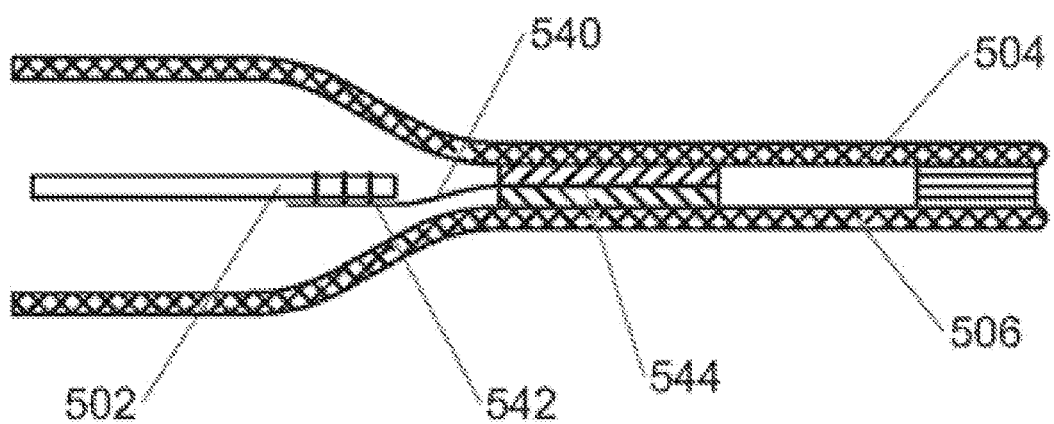
FIG. 8 is a cross-section of a shell containing a heating element secured to the shell according to some embodiments of the present invention.

As previously discussed with reference to at least FIGS. 2A, 4A and 4B, securing strips 317, 371 or securing edges 327 can be provided in some embodiments to facilitate securing the heating element (e.g., 310) to the shell (e.g., 105). With reference to FIG. 8, an exemplary securing strip 540 can comprise a weldable plastic film, for example, a urethane film. A first end 542 of the securing strip 540 can be attached to the heating element 502, for example by sewing. A second end 544 of the securing strip 540 (or securing edge according to alternate embodiments) can be placed between the two sheets 504, 506 and incorporated into the welds between the two sheets. Thus the heater assembly is held in an extended position within the shell, without using stitches, sewing, rivets or grommets that would pierce the flexible material sheets and make the shell difficult to clean.

Figure 9A:
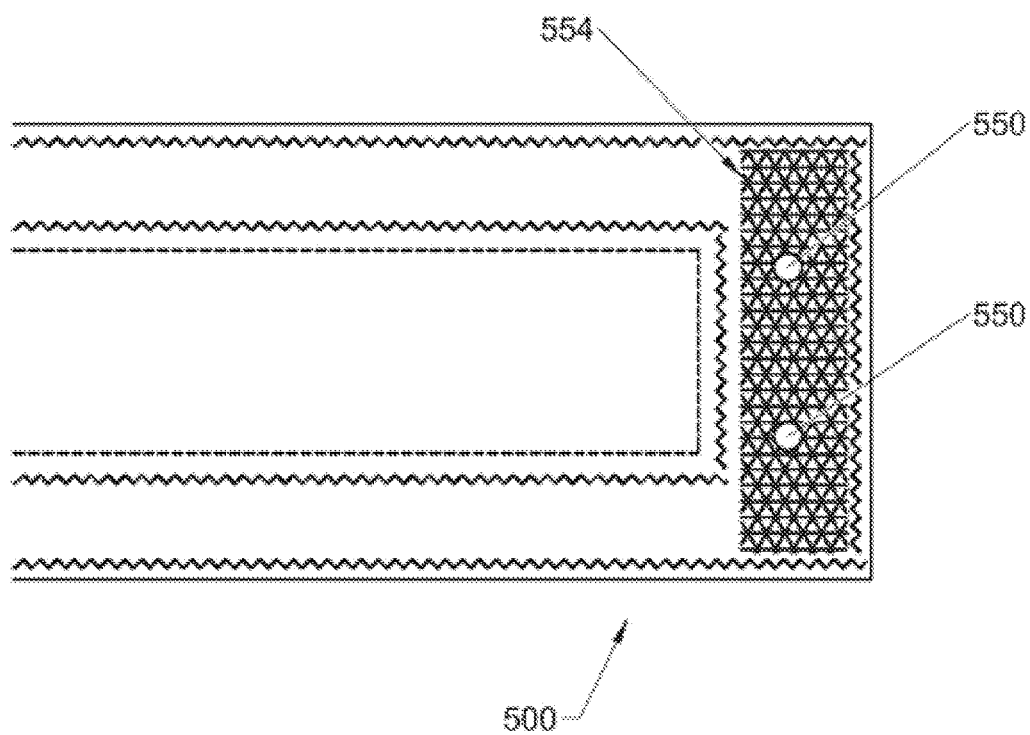
FIG. 9A is a top plan view of a shell containing reinforced hanger points according to some embodiments of the present invention.
Figure 9B:
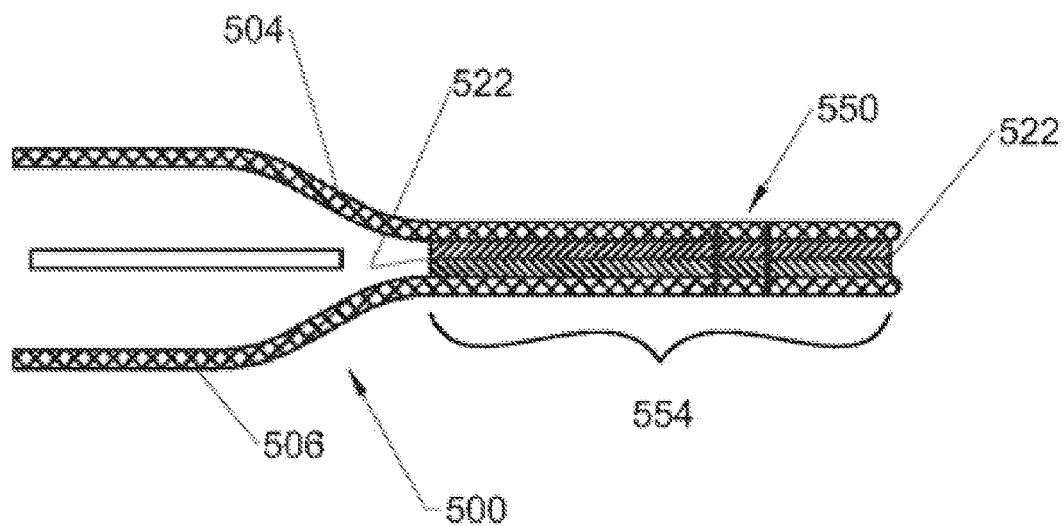
FIG. 9B is a cross-section of the shell of FIG. 9A.

With reference to FIGS. 9A-9B, some exemplary shells 500 provide reinforced hanger points 550 without the use of grommets or another similar mechanism for reinforcement.

As shown, a reinforcing layer 552 extends between the sheets 504, 506 where they are welded at one end about the perimeter of the heating element 502. The reinforcing layer 552 may be formed in addition to strengthening layer of sheets 504, 506. In some embodiments more than one reinforcing layer may be utilized, for example, on opposing ends of the shell 500 or one layer integrated into one of both of sheets 504, 506. The reinforcing layer 552 can in some embodiments comprise one or more pieces of thermally bondable plastic film, for example a urethane film. The reinforcing layer 552 is incorporated into a weld 554 that may extend from near the perimeter of the heating element 502 to near the perimeter of the sheets 504, 506. One or more holes can be punched through both sheets and through the reinforcing layer 552 to create a hanging point 550. The exemplary reinforcing layer 552 reinforces the hanging point 550 without the need for additional grommets that would make the blanket or pad more difficult to clean.

Figure 10A:
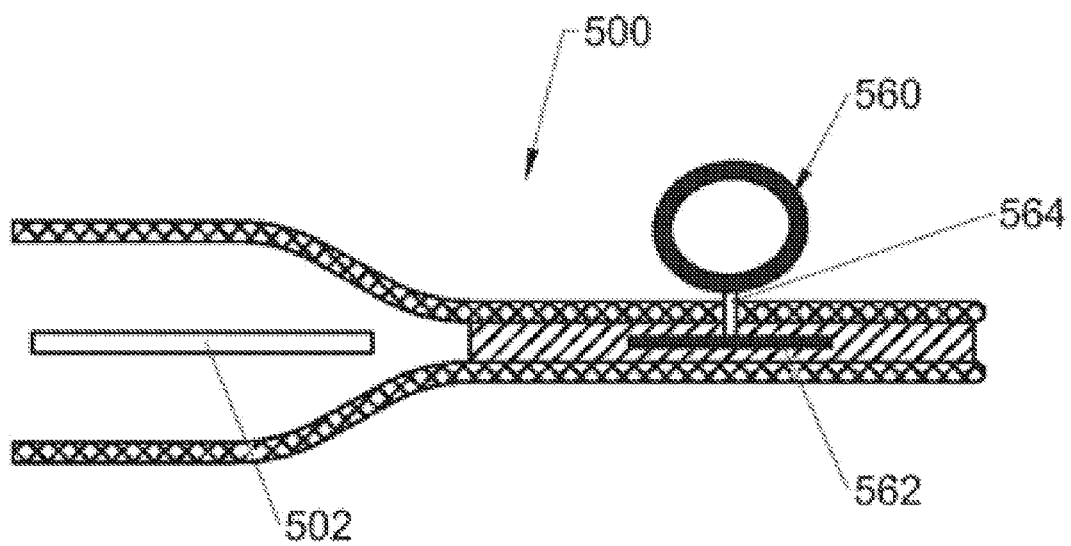
FIG. 10A is a cross-section of a shell containing a heating element, including an attachment point secured to the shell according to some embodiments of the present invention.
Figure 10B:
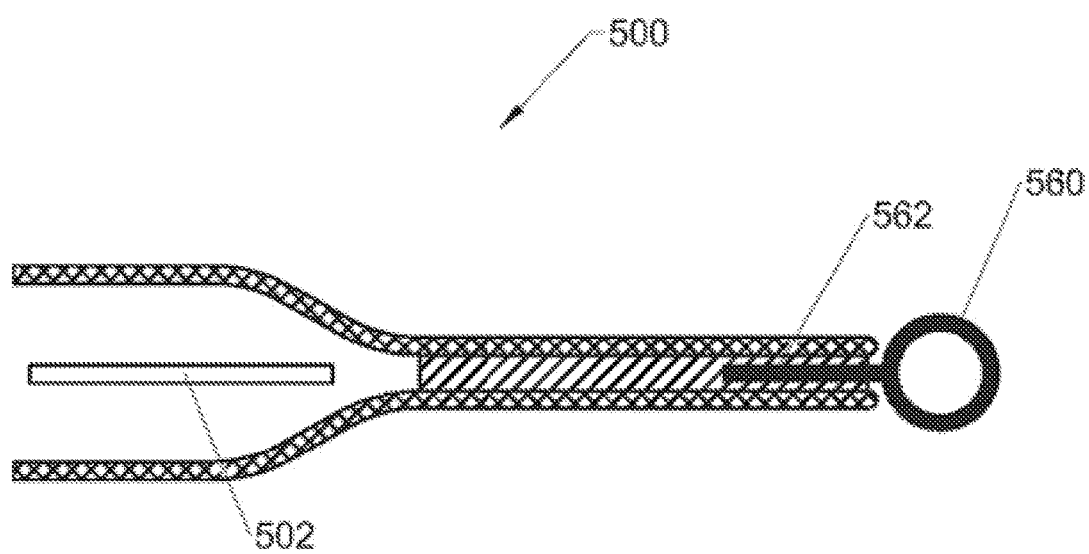
FIG. 10B is a cross-section of a shell containing a heating element, including an attachment point secured to the shell according to some embodiments of the present invention.

With reference to FIGS. 10A-10B, exemplary shells 500 are shown with an incorporated anchor point 560. As shown, the anchor point 560 can in some embodiments be a "ball-shaped" or a "mushroom-shaped" protuberance which can serve as an attachment post on which a strap with holes in it may be secured, for example, the straps of FIGS. 7A-7B. The anchor point 560 can be made of plastic or some other material such as metal. As shown in FIGS. 10A-10B, the anchor point 560 can be molded or otherwise attached to an anchoring layer 562, which in some embodiments comprises a flat piece of thermally bondable plastic material, such as, for example, a urethane material. The anchoring layer 562 can be placed between the two sheets 504, 506 about the perimeter of the heating element 502 and the anchor point 560 can extend from the edges of the sheets as in FIG. 10B or through a hole 564 made in one of the sheets as in FIG. 10A. The sheets 504, 506 can be welded to the anchoring layer 562 to anchor the anchoring layer 562 between the sheets 504, 506 and also to seal the cut edge of the hole 564 or edge of the sheets 504, 506.

In some embodiments, a piece of ribbing or piping can be molded to the edge of an anchoring layer similar to that shown in FIG. 10B. The anchoring layer can then be placed between the two sheets at their edges such that the ribbing or piping protrudes beyond the edges of the sheets. Exemplary ribbing or piping may be plastic or another suitable material such that the ribbing or piping advantageously seals the edges of the shell and creates a soft edge to the warming blanket or pad. Portions of the ribbing or piping may include the anchor point 560.

Figure 11:
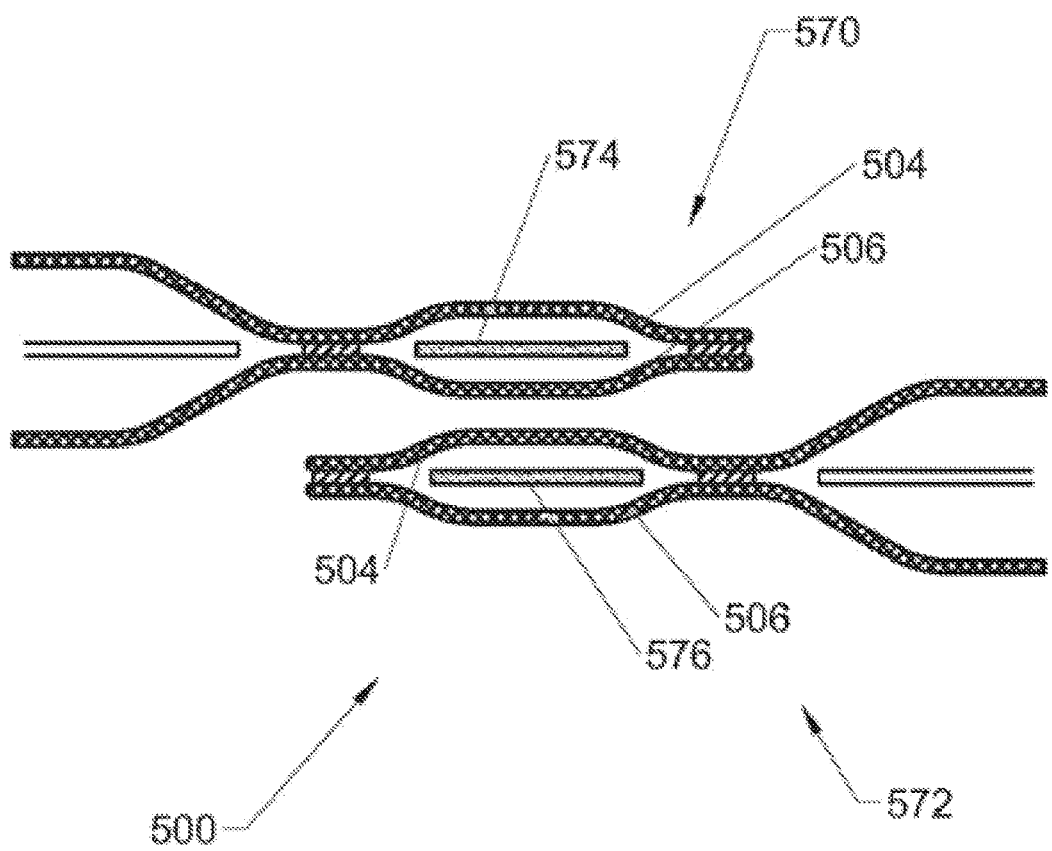
FIG. 11 is a cross-section of two ends of a shell containing a heating element, including a securing magnet.

With reference to FIG. 11, in some embodiments, a warming blanket or pad can be secured to a patient, about a patient, or to a surgical table with one or more magnets 574 and/or ferrous metal pieces. FIG. 11 shows two opposing ends 570, 572 of a single shell 500 and warming blanket or pad configured in a loop according to some embodiments. As shown, a magnet 574 can be fixed in position between sheets 504, 506 at end 570 via appropriately placed welds of sheets 504, 506. Alternately a ferrous metal piece 576 or another magnet can be fixed in position between sheets 506, 504 at end 572 in the same manner as magnet 574. The magnet 574 is placed in a position to mate with ferrous metal piece 576, securing the blanket or pad in place. The metal piece 576 and the magnet 574 are both contained between the sheets 504, 506 and therefore do not complicate the cleaning of the warming blanket or pad.

Embodiments of the heated blanket or pads described herein may be provided as a pad in the form of a heated underbody support. The term underbody support may be considered to encompass any surface situated below and in contact with a user in a generally recumbent position, such as a patient undergoing surgery including heated mattresses, heated mattress overlays and heated pads. Heated mattress overlay embodiments may be identical to heated pad embodiments, with the difference being whether or not they are used on top of a mattress. Furthermore, the difference between heated pad embodiments and heated mattress embodiments may be the amount of support and accommodation they provide, and some pads may be insufficiently supportive to be used alone like a mattress. As such, the various aspects which are described herein apply to mattresses, mattress overlays and pad embodiments, even if only one type of support is shown in the specific example.

Described herein are various embodiments of warming pads that improve patient warming effectiveness by increasing accommodation of the patient into the pad, in other words, by increasing the contact area between the patient's skin and the heated surface of the pad (e.g., heated mattress, mattress overlay). In some embodiments of the pad, as will be further discussed herein, the pad includes not only a heating element, but may also include foam, or could also be air bladders of (e.g., mattress components) that are easily deformable to allow the patient to sink into the pad. This accommodation increases the area of the patient's skin surface in contact with the heated pad and minimizes the pressure applied to the patient at any given point. It also increases the surface contact area for heat transfer and maximizes blood flow to the skin in contact with the heat for optimal heat transfer. Unlike conventional patient warming systems, the accommodation of the patient into the pad is not hindered by a stiff, non-conforming, non-stretching, hammocking heating element. Additionally, in various embodiments, the heating element is at or near the top surface of the underbody support, in thermally conductive contact with the patient's skin, not located beneath thick layers of foam or fibrous insulation.

Various embodiments further provide improved safety. For example, some embodiments provide a heating element that does not produce or reduces "pressure points" against the patient's body, such as against bony prominences, which can occur when a heated pad (or blanket) is stiff.

Figure 12:
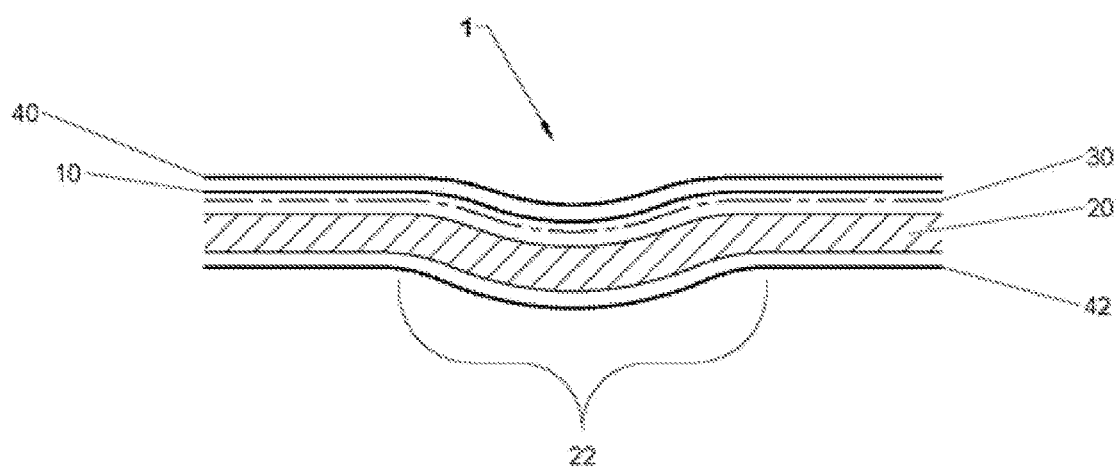
FIG. 12 is a cross sectional view of a heater assembly undergoing deformation in accordance with embodiments of the invention.

FIG. 12 depicts a cross section of a portion of a heater assembly 1. In some embodiments, the heater assembly 1 (e.g., may be same or similar to heating blanket or pad 100, or heating element assembly 350, or any other heaters described herein) including a stretchable fabric heating element 10 (e.g., may be the same or similar to heating elements 310, 502). This example shows the benefits of the stretchable heating element 10, along with a compressible material layer 20 beneath the heating element 10 and bonded to the heating element 10 by a layer of adhesive 30. The heater assembly 1 may include an upper shell 40 and a lower shell 42 (e.g., may be similar to sheets 504, 506). This construction of the heater assembly 1 is favorable because it curves smoothly under pressure from a patient's body (not shown) to stretch into an area of compound curve deformation 22.

In the embodiment shown in FIG. 12 and in several other embodiments, a foam layer 20 is included beneath the heating element 10 (e.g., 310 in FIG. 2A). However, the foam layer 20 may alternatively be described as a layer of compressible material in each of these embodiments and is not limited to foam. For example, the layer of compressible material may comprise gel, stuffing material such as polyester, polyester pellets, bean bag material such as polystyrene beads, air filled compartment, or any material that provides a flexible layer for patient accommodation.

Heat transfer is maximized when the heating element 10 is in conductive thermal contact with the patient. However, as described previously in some embodiments, at least one layer of plastic film is interposed between the heating element 10 and the patient to protect the heating element 10. The one or more layers of thin plastic film may form the upper sheet 40 between the heating element 10 and the patient to introduce minimal thermal resistance to heat flow. In certain embodiments of this invention the fabric heating element 10 may be laminated between two layers of thin (<0.004 in.) and preferably stretchy (e.g. urethane or polyvinyl chloride) plastic films. Laminating a thin layer of plastic film directly onto each side of the heating element 10 protects the heating element 10 fabric from damage by liquids and oxidation. Thin layers of plastic film are sufficient to protect the heating element 10 from liquid and gases, add minimal if any stiffness to the construction, and still allow the heating element 10 to stretch and return to its original shape. This is in contrast to some other conductive fabrics which may require lamination between two thick layers of plastic film in order to provide structural strength and durability, resulting in a stiff and non-stretchable heater.

In some embodiments, the heating element 10 is coated with one or more thin layers of elastomeric materials such as rubber or silicone. The layers of elastomeric material protect the heating element 10 material from damage due to moisture and oxidative chemicals such as hydrogen peroxide. The layers of elastomeric material also provide an electrically insulating layer over the heating element 10 material.

In some embodiments the heating element 10 is also used as a grounding electrode during electro-surgery, the upper layer of elastomeric material forms a second dielectric layer between the patient and the heater, adding to the safety of the device should the outer shell material 40, 42 be cut or pierced. The second dielectric layer prevents a direct electrical contact between the patient and the grounding electrode (e.g., 10).

The pressure relief provided by the pad is maintained by allowing maximal accommodation (allowing the patient to sink into the support) without the heating element assembly creating a "hammocking" force. By allowing maximal accommodation and avoiding hammocking, cutaneous blood flow is maximized at the pressure points, which minimizes the risk of pressure ulcers. The pressure needed to collapse capillaries is said to be 12 to 32 mm Hg. By allowing maximal accommodation and avoiding hammocking, cutaneous blood flow is generally maximized. By maximizing blood flow, the ability of the skin and tissue to absorb heat from the heating element 10 and transfer it to the rest of the body is also maximized. Further, by allowing the patient to sink (accommodation) into the heater assembly 1, the surface area of the heating element 10 in contact with the patient is maximized and thus heat transfer is maximized.

Figure 13:
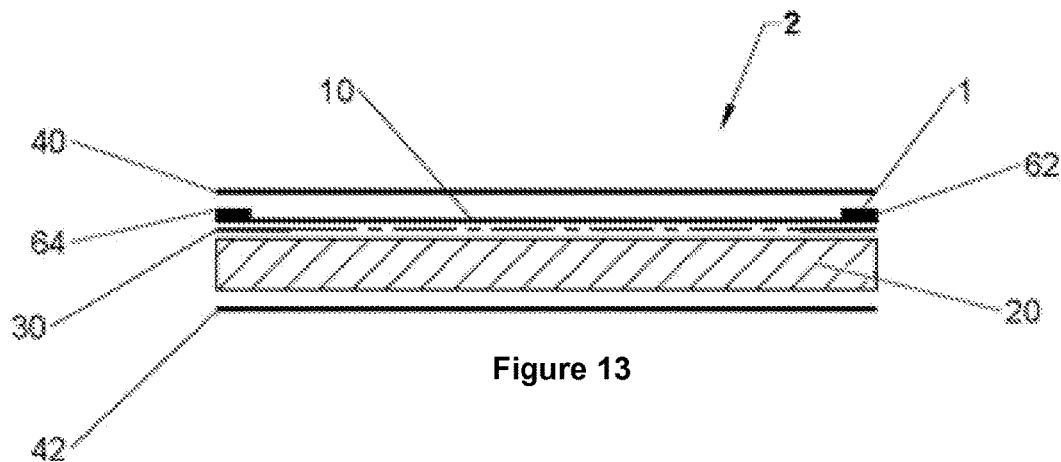
FIGS. 13, 13A and 13B are cross sectional views of a heated mattress overlay or pad in accordance with embodiments of the invention.

When not stretched, fabric heating elements 10 as described herein provide an even heat output or Watt density across their surface, unless they are folded or wrinkled, doubling or tripling the heating element 10 layers in the folded or wrinkled portion. The entire heating element 10 may have a relatively low Watt density, such as less than 0.5 watts per square inch, for example. Therefore, it is preferable to prevent local wrinkling of the heating element 10. An embodiment of a heated pad 2 in the form of a heated underbody support, a heated mattress, or a heated mattress overlay includes a heater assembly 1 and a compressible material layer (e.g., foam layer) 20 and having reduced wrinkling or folding is shown in FIG. 13. It should be noted, however, that whether a unit is described as a heated mattress, heated mattress overlay or heated pad is largely unimportant, and most embodiments could be used variously as heated underbody supports. While a heated mattress overlay or blanket may have no layer of padding or may have a thinner layer of padding, a heated pad typically has padding that may be thin or thick, a heated mattress may have an even thicker layer of padding. As such, various embodiments of the pad may be used alone, in the manner of a mattress, or on top of a mattress, in the manner of a mattress overlay. Descriptions relating to heated mattress overlays therefore also apply to descriptions of heated mattresses and heated pads, and vice versa.

The compressible material layer 20 (e.g., FIG. 13) may be a single layer or may be a stack of materials that includes a layer of foam. This stack could include foam layers of different densities, different accommodation properties, different stiffness or different polymers. Additionally, the stack of materials can include other materials such as woven or non-woven fabrics or films, to achieve other characteristics such as lateral stiffness or durability and strength. The term compressible material layer 20 therefore refers generally to single layers of foam as well as multilayered stacks that include one or more layers of foam and may include other materials. Also, the layer of foam may alternatively be a layer of compressible material as described above.

As shown in FIG. 13, the attachment of the heating element 10 to the compressible material layer 20 may be achieved by adhesive bonding 30 across the entire interface between the two. The bond may be made with an adhesive comprising a pressure-sensitive adhesive without a reinforcing fiber or film carrier. Since the compressible material layer 20 is preferably flexible, stretchable and compressible, such a bonding made with such an adhesive does not alter the flexibility and stretch-ability of the heating element 10 or heated mattress overlay or pad 2. Alternately, the heating element 10 may be attached to the compressible material layer 20 only along one or more of the edges 12, 14, 16, 18 (16 and 18 not shown in FIG. 13, but similar and generally perpendicular to edges 12 and 14). In some embodiments the heating element 10 may be attached to the compressible material layer 20 only along one or more edges such as along two opposing edges such as edges 12, 14, or in an intermittent pattern.

Figure 14:
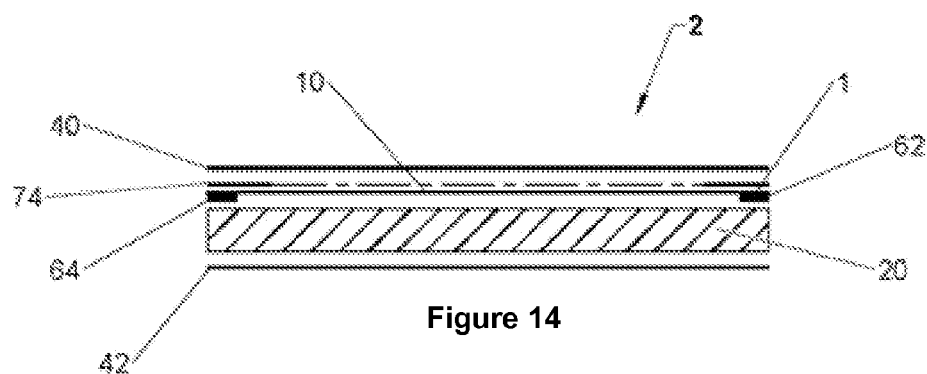
FIG. 14 is a cross sectional view of a heated mattress overlay or pad in accordance with embodiments of the invention.

FIG. 14 depicts a cross section of a portion of an alternative embodiment of a heated pad 2, in which the fabric heating element 10 and the overlaying plastic film layer comprising an upper shell 40 include a sacrificial layer of fabric or foam 74, inserted there between. The sacrificial layer of fabric or foam 74 is preferably treated with manganese dioxide (MnO2) to act as a catalyst in the destruction of hydrogen peroxide cleaning fluid vapor that may permeate the upper shell material 40 and enter the shell where it can damage the electrical components.

Figure 15:
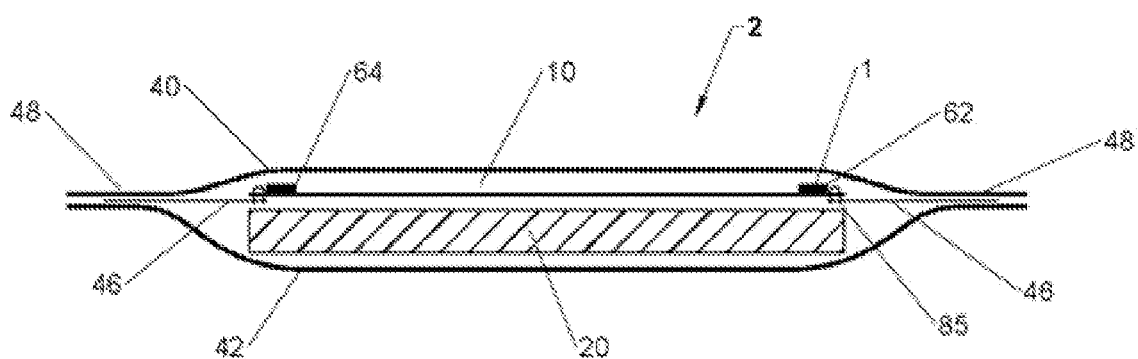
FIG. 15 is a cross sectional view of a heated mattress overlay or pad in accordance with embodiments of the invention.

An alternative embodiment is shown in the heated pad 2 which is shown in FIG. 15. In this embodiment, the fabric heating element 10 is anchored to the shell including the upper shell 40 and the lower shell 42 along its edges and thus held in an extended and wrinkle-free condition. Anchoring strips 46 comprised of plastic film or a suitable alternative are attached along the edges of the heating element 10, preferably by sewing to form a sewn connection 85, though other forms of attachment may be used such as adhesive bonding. The anchoring strips 46 extend along all four edges of the heating element 10 to form a peripheral bond 48. Alternatively, the anchoring strips 46 may extend along only one pair of opposing edges such as edges. The anchoring strips 46 may be made of the same material as the shells 40, 42, such as plastic film, and therefore can be bonded around the periphery of the heated pad 2, being sandwiched between and incorporated into the bond between the upper shell 40 and the lower shell 42.

Hydrogen peroxide ($H_2O_2$) disinfecting solutions have recently been introduced into the operating room and hospital to clean and sanitize medical equipment. $H_2O_2$ is a well-known, powerful oxidizing agent that kills bacteria and viruses in a mechanical way that cannot lead to resistant strains. The oxidation reaction causes the $H_2O_2$ to break down into water and oxygen, two harmless, or less harmless by-products. The problem is that $H_2O_2$ vapor is also highly oxidizing for electrical components, including flexible heater materials (including polypyrrole), metal bus bars and conductive metal coatings such as silver on fabric or thread. There is a need for better protection of the sensitive electrical components from oxidation by $H_2O_2$ and other oxidizers.

In some embodiments, urethane film may be used as the shell 40, 42 material for the heated pad 2 or related blankets, because of its strength, flexibility durability and response to heat sealing. Unfortunately, although urethane film may be good for providing a water-resistant and encapsulating shell 40, 42, urethane film is relatively permeable to hydrogen peroxide vapors, allowing the highly oxidizing vapors to enter the heated pad 2 or a related heated electric blanket. Once inside, the peroxide vapors attack any oxidizable material. These vapors can cause oxidation and failure of electrical components, especially polypyrrole. Other plastic films such as PVC are much less permeable to peroxide vapor than urethane. Since peroxide is becoming more and more common as a disinfectant for operating room and other hospital use, a way of protecting vulnerable internal components from oxidation due to peroxide is needed.

In some embodiments, the heated pad 2 or the related heated electric blankets incorporate certain materials that can protect the polypyrrole heater (e.g., heating element 10) and other oxidizable electrical components from oxidizing agents such as hydrogen peroxide ($H_2O_2$) disinfecting solutions. In some embodiments, a catalyst to accelerate hydrogen peroxide decomposition may be coated on or impregnated into an element within the shell 40, 42, or on the interior surface of the shell 40, 42.

In some embodiments, sacrificial materials may be included in the internal construction that can be preferentially oxidized. Sacrificial materials may be organic materials such as cellulose. For example, sacrificial materials such as one or more sacrificial layers 74 of cotton, linen or paper, as shown in FIG. 14, may be added to the inside of the heated pad 2 or the related heated electric blanket so that the peroxide vapors preferentially attack and oxidize the sacrificial material. Other oxidizable sacrificial materials may be used. In the process of oxidizing these sacrificial materials, the peroxide breaks down into inert (e.g., less corrosive, less problematic) water and oxygen before it can attack the electrical components. The catalyst for accelerating hydrogen peroxide decomposition may decompose all, substantially all, or the majority of the hydrogen peroxide vapors before they reach the electrical components, depending on how the catalyst is incorporated into the particular apparatus.

In some embodiments, materials that are known to be catalysts for the breakdown reaction of peroxide to water and oxygen may be added. For example, manganese dioxide ($MnO_2$) powder may be added to one or more of the sacrificial layers 74 in FIG. 14, or the compressible material layer 20, the inside surface of the shell 40, 42, or adhered directly to any suitable component of a heater assembly 3 (e.g., FIG. 25) by an applied coating, by impregnation into, by adhesive, or by any other suitable process. Catalysts for the breakdown reaction of peroxide to water and oxygen may be added to any heater assembly, or any suitable component of any of the heater assemblies described herein.

In some embodiments, the insoluble manganese dioxide powder may be suspended in water and the sacrificial layer 74 of fabric or foam can be dipped in this water/manganese dioxide powder suspension to evenly disperse the powder throughout the sacrificial layer 74 of fabric or foam when the water evaporates. In some embodiments, a small amount of methyl cellulose can be added to the water/manganese dioxide powder suspension in order to increase the duration of the suspension time of the powder in water. The small amount, or sufficient amount of methyl cellulose to increase the viscosity of the water and manganese dioxide suspension to between 10 and 120 centipoise. The methyl cellulose may also act as a binding agent, improving adherence of the manganese dioxide powder to the fabric, foam or other material. Other binding agents, and/or suspension improvers besides methyl cellulose may be used. Adding too much binding agent (e.g., greater than 120 centipoise) can cause the binding agent to completely encapsulate the manganese dioxide powder when it dries, and too little (e.g., less than 10 centipoise) will not hold the powder in suspension very long. Other carriers besides water may also be used.

In some embodiments, the one or more sacrificial layers 74 of manganese dioxide impregnated fabric or compressible material layer 20 may be added to the inside of the pad 2 or related heated electric blanket so that the catalyst can preferentially attack the peroxide vapors and neutralize them to water and oxygen, before they can damage the electrical components. Other liquids are anticipated for suspending the manganese dioxide powder. Examples of catalysts that can be used in place of manganese dioxide powder include: silver, platinum and transition metal salts. Other catalysts may also be used. In some embodiments the catalysts may be added to another feature of the pad 2 or the related heated electric blanket, and to a material other than fabric or foam.

The effectiveness of these measures for preventing the oxidation and degradation of the heater fabric (e.g., heating element) and other mattress or blanket components by peroxide vapor was tested. During testing similar squares of heater material with bus bars attached were sealed into shells of urethane film. The heaters (e.g., heating pad or blanket) were then placed into a chamber that continuously exposes the shell to peroxide vapor. Over the course of 9-12 days, the change in resistance of the heater material was measured and correlated with the degradation of the conductance of the heater material. Over the course of 9 days of exposure to peroxide vapor, the resistance of unprotected polypyrrole heater material increased from 58.4 to 238.2 ohms on the square. The significant increase in resistance, indicates that the conductivity of the unprotected conductive heater material (e.g., heating element 10) was rapidly degraded by the peroxide vapors.

Over the course of 12 days of exposure to peroxide vapor, the resistance of heater assemblies that included two layers of sacrificial cotton fabric inside the shell, increased from 53.5 to 84.8 ohms on the square. Over the course of 12 days of exposure to peroxide vapor, the resistance of heater assemblies that included two layers of polyester fabric impregnated with manganese dioxide inside the shell, did not increase resistance at all (52.8 to 52.8 ohms on the square). The MnO$_2$ was very effective as a catalyst neutralizing the peroxide vapor before it could destroy the heater assembly. The sacrificial layer of cotton fabric was also quite effective in protecting the heater assembly but less so than the MnO$_2$.

This disclosure of using MnO$_2$ or sacrificial cellulose layers to protect oxidizable components, especially electrical components, is not limited to heated underbody supports (e.g., heated pads) 3 and heating blankets. In some embodiments, other medical equipment (e.g., apparatus) including electrical components such as patient monitors, patient monitoring electrodes, patient monitoring sensors and medical equipment control circuits may be protected from oxidation and damage by peroxide vapors or liquid, by incorporating MnO$_2$ or sacrificial cellulose layers into the equipment, as disclosed in this application.

Some embodiments maintain the heating element 10 in an extended and unwrinkled condition. It may be preferable in order to avoid hot spots, that more than one heating element 10 anchoring embodiment be used simultaneously. To maintain flexibility, conformability and stretchability, the upper and/or lower shell 40, 42 may be adhered to the heating element 10 or the compressible material layer 20, across their broad surfaces as shown, for example, in FIG. 14, or may not be so adhered. However, in some embodiment the heating element 10 can be bonded to the upper shell 40, for example. This may be advantageous for minimizing wrinkling of the heating element 10 or plastic film layer of the shell 40, 42.

The compressible material layer 20 (or layer of compressible material) supporting the heater assembly 1 in certain embodiments of this invention could be almost any thickness that is advantageous for the given application (for example, 0.5-6.0 inches). The compressible material layer 20 may be uniform in thickness and density or it may be contoured in thickness, shaped, scored or segmented according to areas of different densities.

Figure 16:
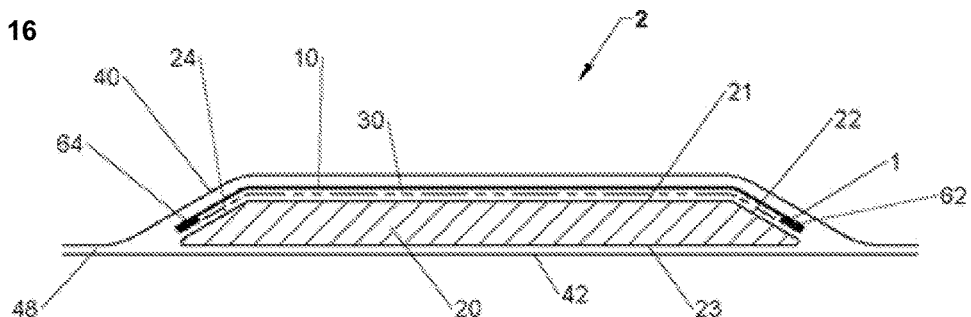
FIG. 16 is a cross sectional view of a heated mattress overlay or pad in accordance with embodiments of the invention.
Figure 17:
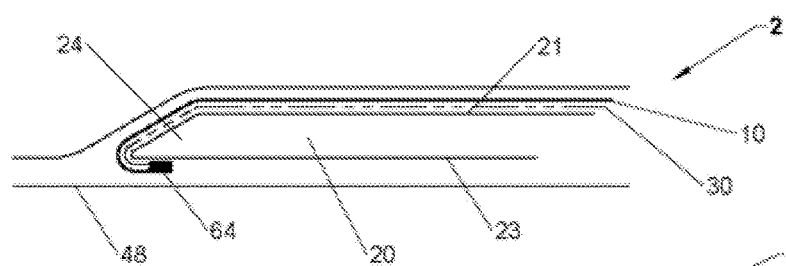
FIG. 17 is a cross sectional view of a heated mattress overlay or pad in accordance with embodiments of the invention.
Figure 18:
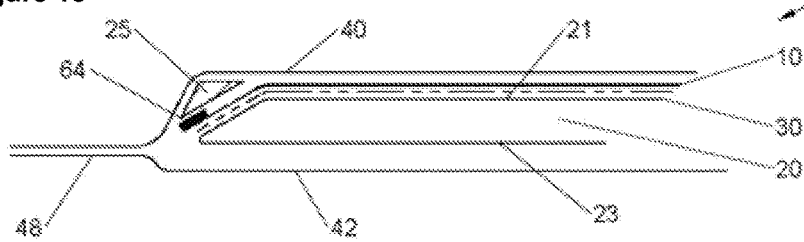
FIG. 18 is a cross sectional view of a heated mattress overlay or pad in accordance with embodiments of the invention.

As shown in FIGS. 16-18, the portions of the heating element 10 attached to bus bars 62, 64, which may include any of the features described with respect to bus bars 315. In the exemplary embodiment of FIGS. 16-18, bus bars 62, 64 are preferably bonded to the compressible material layer 20 along beveled ends 22, 24. Locating the bus bars 62, 64 on the beveled ends 22, 24 of the foam layer 20 provides some protection of the bus bars 62, 64 from mechanical stress when patients are sitting or lying on the heated pad 2. Alternatively, to provide additional protection to the bus bars 62, 64, the heating element 10 may be wrapped around the compressible material layer 20 and onto a bottom surface 23 so that the bus bars 62, 64 are located under the foam layer beveled ends 22, 24 and attached to the bottom surface 23 as shown in the cross section shown in FIG. 17, for example. In a further alternative shown in FIG. 18, the beveled piece of compressible material that is removed from the compressible material layer 20 or any other triangular or wedge shaped piece of compressible material of complementary size and shape to fit the space may be bonded over the heater assembly's bus bars 62, 64, along the beveled edges 22, 24 of the compressible material layer 20 to form a filler 25, to fill in the beveled space and protect the bus bars 62, 64. The compressible material filler 25 may be sized such that, when in place above the bus bars 62, 64, the horizontal upper surface of the heated pad 2 above the central, non-beveled portion of the compressible material layer 20, is level with the horizontal upper surface of the overlay 2 above the beveled end 24. In these embodiments the heating element 10 extends across an upper surface 21 of the compressible material layer 20, and the bus bars 62, 64 are away from and lower than the upper surface 21. In this way, the bus bars 62, 64 may be physically protected from damage by bonding them onto or beneath the beveled edges 22, 24 of the compressible material layer 20, where they are effectively recessed from the upper surface 21 of the foam layer 20. The beveled edges 22, 24 of the compressible material layer 20 allow the bus bars 62, 64 to be optionally covered with a compressible material filler 25 to act as a protective barrier in this location for added protection, without adversely affecting the look of the smooth top surface of the heated pad 2, thereby basically filling the bevel space with a compressible material filler 25 to create an overall rectangular cross sectional shape.

In some embodiments, the combination of conductive fabric heating elements 10 made from flexible and stretchable material, bus bars 62, 64 attached near opposing edges 12, 14 of the heating element 10, one or more temperature sensors and a controller, comprises a heater assembly 1 according to some embodiments. The heater assembly 1 may be secured to a compressible material layer 20 such as foam and may be covered with a water-resistant shell 40, 42 that is preferably made of a stretchable plastic film such as urethane or PVC, however, other film materials and fiber-reinforced films are anticipated.

Figure 19:
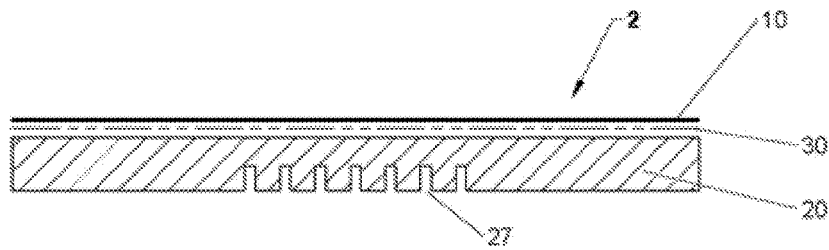
FIG. 19 is a cross sectional view of a heated mattress overlay or pad with partial thickness cuts or channels in the foam layer in accordance with embodiments of the invention.

In some embodiments, a portion of the compressible material layer 20 is thinned or scored in an area, from one lateral edge to the other of the area, with the area located to overlie the location of transition from one cushion of an operating table to the adjacent cushion under normal conditions of use. Preferably the thinning or scoring is on the bottom surface 23 of the compressible material layer 20 and therefore away from the patient contact top surface 21. Since operating room tables are designed to flex at this location between the operating table cushions, a thinned compressible material layer 20 at the location of transition between cushions will aid in flexion of the heating element 10 and reduce the chances of the heating element 10 wrinkling during flexion. Alternatively, the compressible material layer 20 could be scored or cut or otherwise have one or more gaps or channels completely through or partially through its thickness on the bottom surface 23 at the flexion locations or other areas where added flexibility may be desirable, as shown in FIG. 19, for example. In the embodiment shown, multiple small channels 27 are present in a portion of the compressible material layer 20 where the compressible material layer 20 is thinner. These channels 27 may extend across the compressible material layer 20, from one end to the opposing end, such as across the width or the length of the compressible material layer 20, such as in a direction parallel to and aligned with the transition between operating table cushions. In use, the pad 2 may be positioned over a table or bed with which it is designed to be used such that the channels are located over the flexion locations of the table or bed. The table or bed may then be adjusted by bending at a flexion point (such as to raise or lower a patient's upper body or legs by bending or extending the patient at his or her hips) and the compressible material layer 20 of the heated pad 2 can bend easily at this location due to thinness or scoring at the location of flexion, while the heating element 10 can likewise bend without wrinkling or folding due to its flexibility and elasticity.

In some embodiments, and as shown in FIG. 19, the compressible material layer 20 may be thinned or scored or have gaps or channels 27 longitudinally in order to increase flexibility for bending the heated pad 2 around a longitudinal axis such as a long axis of a body. This may be advantageous to aid in wrapping the heated pad 2 around a patient being positioned within a "bean bag" or "peg board" positioner. The longitudinal thinning or scoring or presence of gaps or channels 27 allows the heated pad 2 to be wrapped around the dependent portion of the patient, increasing the area of surface contact between the heating element 10 and the skin while avoiding wrinkling of the heating element 10 due to the bending of the compressible material layer 20.

Figure 20:
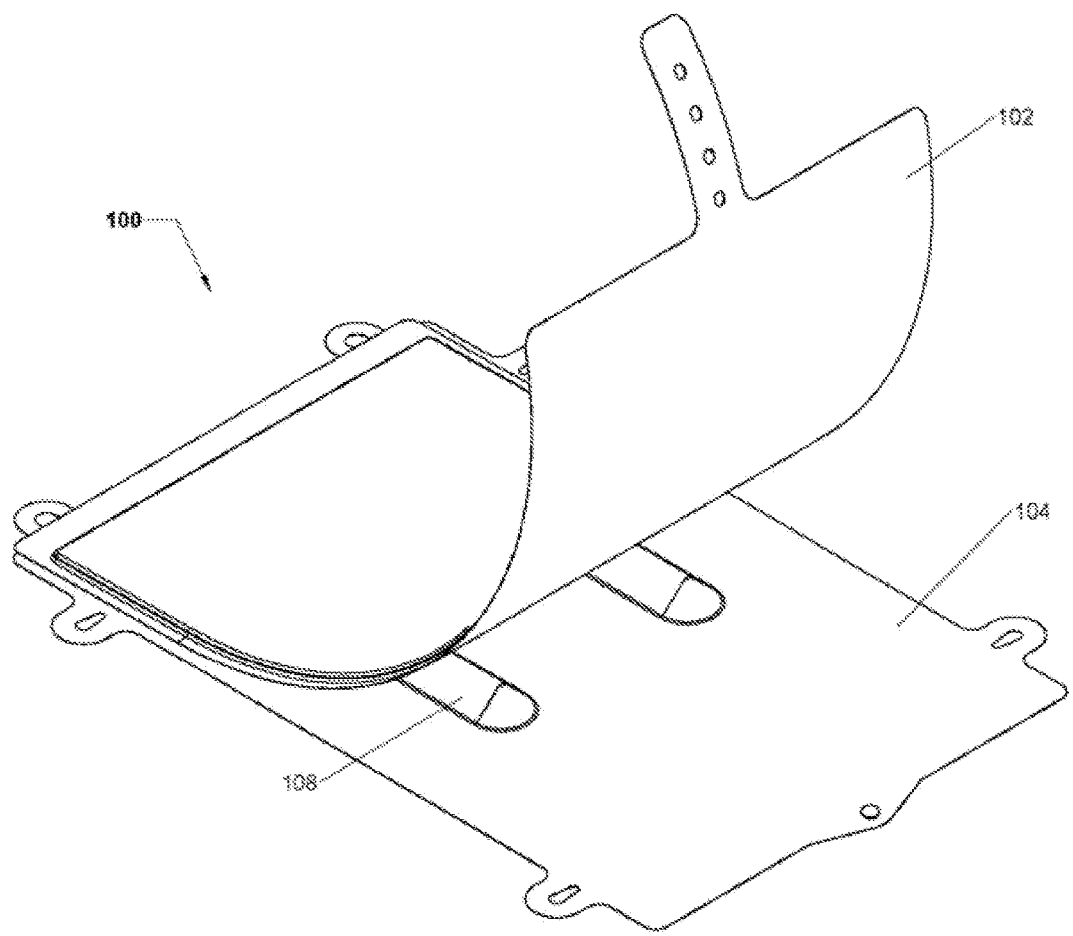
FIG. 20 is a perspective view of a heated pediatric mattress overlay or pad in accordance with embodiments of the invention.
Figure 21:
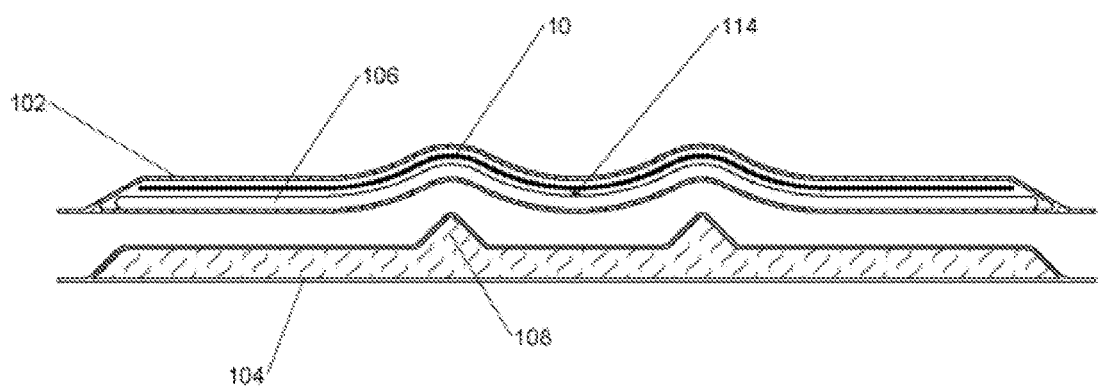
FIG. 21 is a cross sectional view of a heated pediatric mattress overlay or pad in accordance with embodiments of the invention.
Figure 22A:
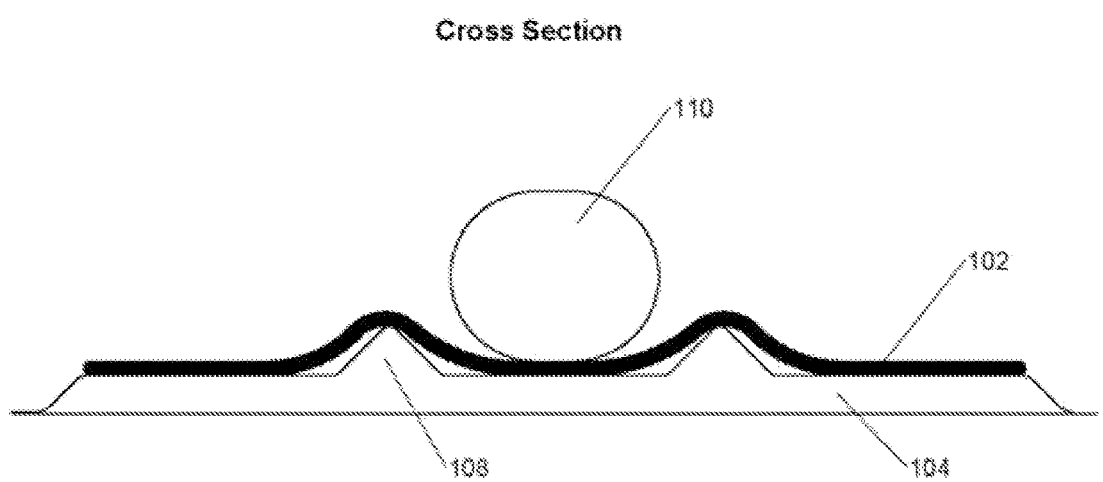
FIG. 22A-D is a cross sectional view of a heated pediatric mattress overlay or pad in accordance with embodiments of the invention.
Figure 22B:
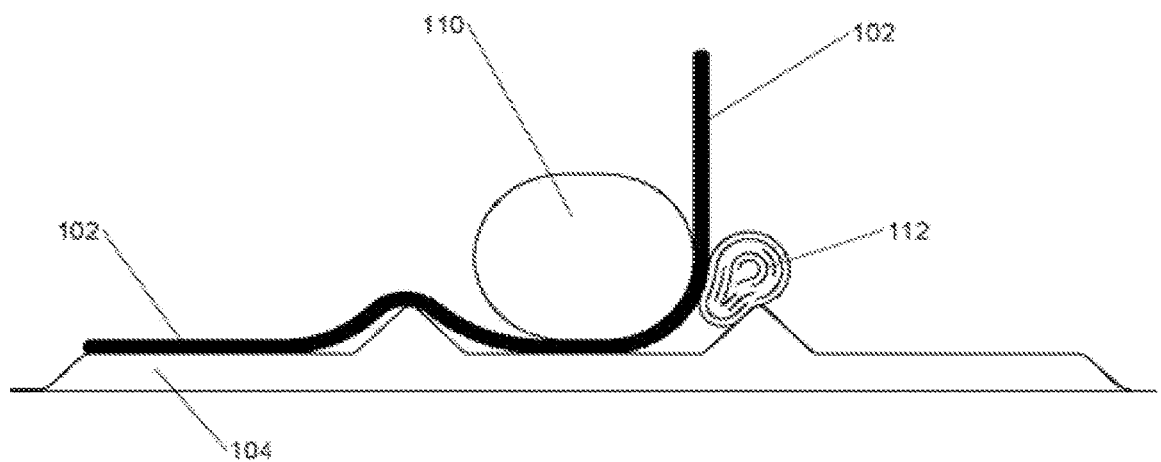
Figure 22C:
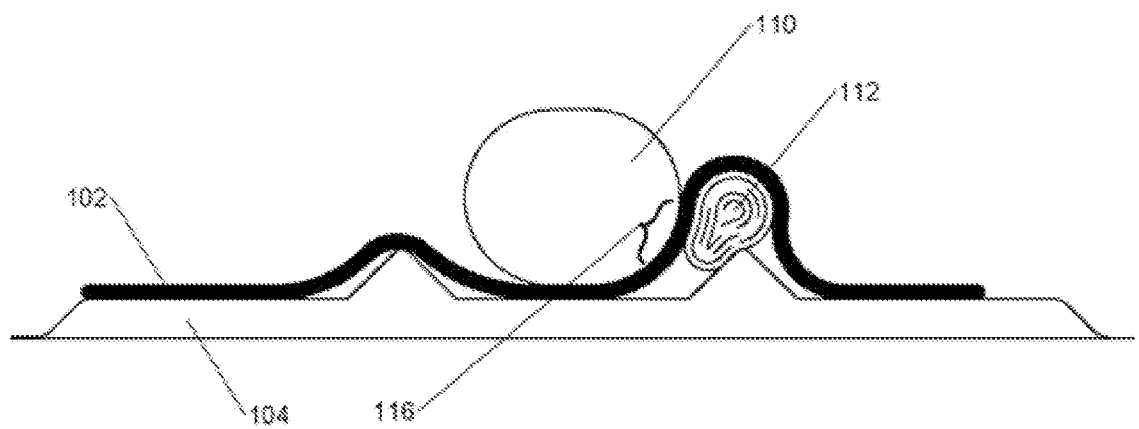
Figure 22D:
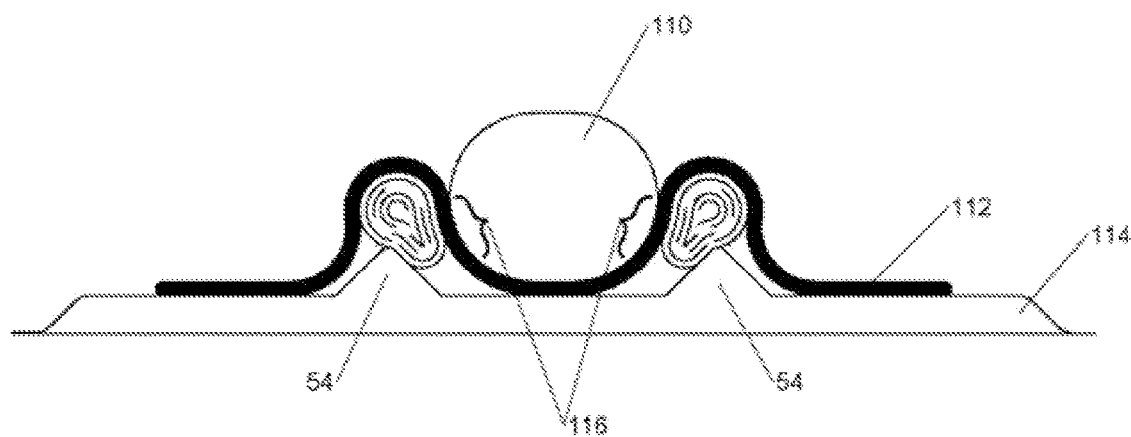

In some embodiments, a heated mattress for pediatric use 100 may include an upper heated layer 102 that is separate from the lower base layer 104 as shown in FIGS. 20, 21 and 22 A-D. The upper heated layer may also include a layer of thermal insulation material 106, preferably located on the underside of the heater element 10, away from the patient contact surface. Preferably the thermal insulation layer 106 is a high-loft fibrous insulation, for example Thinsulite™ (3M, St. Paul, Minn.).

As shown in FIG. 20, and in some embodiments, the upper heater layer 102 is attached to a lower base layer 104 in a way that maintains the alignment of the upper heated layer 102 as it rests on the lower base layer 104 yet allows maximal independent flexion between the two layers. The preferred attachment location between the two layers 102, 104 is at the foot end periphery of the mattress 2. Alternately, it could be that the two layers 102, 104 are attached to each other at the head end or in a central region such as along a longitudinal centerline. These examples are not meant to limit other areas of attachment between the two layers 102, 104. The heater layer 102 is not bonded to the base layer across their entire opposing surfaces or around their entire peripheries. The two layers 102, 104 are free to fold and bend substantially independently of one another (FIGS. 20, 21 and 22A-D).

Maintaining the alignment of the two layers 102, 104 helps assure that the heater layer 102 does not slip, perhaps dropping the patient off of the bed. Surgical mattresses are frequently attached to the surgical table and in certain embodiments of this invention, preferably only the base layer is attached to the table. The attachment between the two layers 102, 104 may be secure enough to assure that the upper heated layer 102 cannot slide independently of the base layer 104.

In some embodiments, the base layer 104 may include two or more elongated longitudinal air bladders 108 near the side edges. The air bladders 108 can be inflated to elevate the sides of the heated layer to a position proximate the side of the patient.

If the attachment between the two layers is not in the longitudinal midline, patient-positioning rolls may be placed under the heated layer to maintain maximal heat transfer characteristics while allowing complex patient positioning. For example, small rolls of towels are frequently placed under the chest/shoulder blades of very small babies in order to put their back into extension and improve access to their upper abdomen. If this positioning roll is placed above the standard heated mattress, the roll lifts half of the patient's body off of the heated surface. Naturally this markedly reduces the heat transfer and capacitive grounding ability of the mattress to the patient. In contrast, this invention allows the positioning roll to be placed under the upper heated layer and the heater thus stays in conductive thermal contact with the entire posterior surface of the patient also maximizing grounding contact.

It has been shown that for optimally safe and effective electric mattress warming, it is believed that the control temperature sensor 114 (FIG. 21) desirably is touching the patient. Therefore, the control temperature sensor is preferably located near the longitudinal midline of the mattress, where the patient is most likely to lay as shown in FIG. 15. It is easy to assure control sensor contact with an adult patient because they cover most of the surface of the mattress (on a narrow operating table). However, small pediatric patients can easily be mal-positioned on the mattress and thus inadvertently fail to contact the control temperature sensor.

In some embodiments, the flexible heating element 10 itself may comprise a temperature sensor. In such embodiments, the flexible heating element 10 is formed of a material having a resistance that varies with temperature. The controller may determine the temperature of the flexible heating element 10 by measuring the resistance or change in resistance in the power supply circuit. The resistance of the heating element 10 may also be used to determine the Watt density output of the heating element 10. Thus, the heating element resistance measurement may be used as a control parameter by the controller to control or adjust the Watt density output of the heated underbody support 2 as desired.

The combination of conductive fabric heating elements 10 made from flexible and stretchable material, bus bars 62, 64 attached near opposing edges 12, 14 of the heating element 10, one or more temperature sensors 110 and a controller, comprises a heater assembly 1 according to some embodiments. The heater assembly 1 may be secured to a compressible material layer 20 such as foam and may be covered with the water-resistant shell 40, 42 that is preferably made of a stretchable plastic film such as urethane or PVC, however, other film materials and fiber-reinforced films are anticipated.

To assure accurate patient positioning relative to the control temperature sensor, this invention preferably includes two or more substantially elongated positioning members 108 that protrude upward between 0.75 and 2.5 inches from the upper surface of the base layer (FIGS. 14, 15, 16A). The elongated positioning members 108 are preferably made of a compressible foam material. The elongated positioning members 108 are preferably triangular in cross-section, are 4-12 inches long and positioned 5 to 8 inches apart (2.5-4 inches from the midline) in the region of the mattress the corresponds to the location of the patient's torso and legs.

These parallel elongated positioning members 108 project upward into the upper heated layer, causing the upper heated layer to form a trough between the positioning members. The midline trough naturally accommodates the baby's body and centers it on the midline (FIGS. 15, 16). If the baby is not centered in the midline of the trough, the foam positioning members 108 will cause the baby to be visibly contorted, alerting the surgical staff that repositioning is required.

In addition to the warming features described herein, in some embodiments and as shown in FIG. 13, the heating element 10, which is already in close proximity to the underside of the patient, is a capacitive coupling grounding electrode 10. By using the heating element material 10 as the grounding electrode 10, there is no competition to determine which technology is going to be in the most advantageous position—close to the patient's skin. Both technologies get the same advantageous location. Using a single piece of conductive material, preferably a stretchable conductive or semi-conductive fabric as the heating element 10 and grounding electrode 10, also minimizes the negative effects of multiple layers of materials and laminates being interposed under the patient, which can cause hammocking, thereby reducing the pressure off-loading abilities of the mattress. The fewer the layers of material, the more stretchable and flexible the construction. Avoiding constructions that involve layers of fabric and film to be bonded together forming laminates is performed in order to optimize stretchability and flexibility.

A semi-conductive polymer such as polypyrrole is advantageous in that it is a preferential RF energy absorber. Polypyrrole can also be polymerized onto fabric and in the process coats each individual fiber, retaining the flexibility and stretchability of that fabric. The polymerization process results in a bond between the fiber and the polymer that is inseparable. This is in contrast to electrically conductive composites made from powdered or vaporized carbon or metals that may be applied to the surface of relatively non-stretching fibers and fabrics such as woven nylon, because such composites will flake off with repeated flexion and stretching. Polypyrrole is, therefore, a preferable conductive material for heaters and grounding electrodes that are to be positioned under a patient because it allows flexion and stretching so that the patient can sink optimally into the support surface below the heating element and/or grounding electrode (e.g., 10).

Figure 13A:
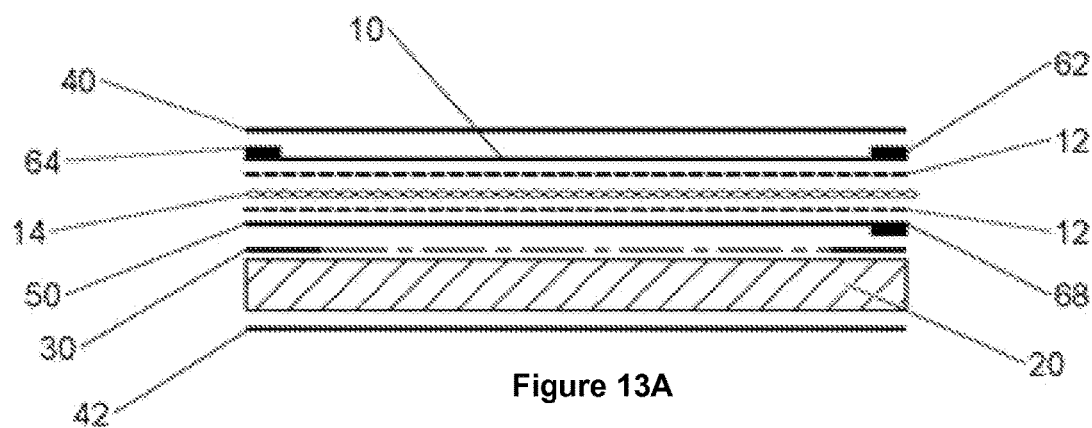

As shown in FIG. 13A, in some embodiments the grounding electrode 50 is a separate layer of material positioned near and parallel to the heater 10. In this case, the grounding electrode 50 may advantageously be made of a semi-conductive polymer such as polypyrrole irrespective of what the material the heating element 10 is made. The heating element 10 and grounding electrode 50 may be electrically insulated from each other by applying a coating of elastomeric material 12 such as silicone or rubber to one or both conductors. A layer of electrically insulating material 14 such as fabric, film or foam may be interposed between the heating element 10 and grounding electrode 50. Preferably these layers of electrically insulating materials are not all bonded together into a laminate that would add unnecessary stiffness to the support surface.

Figure 13B:
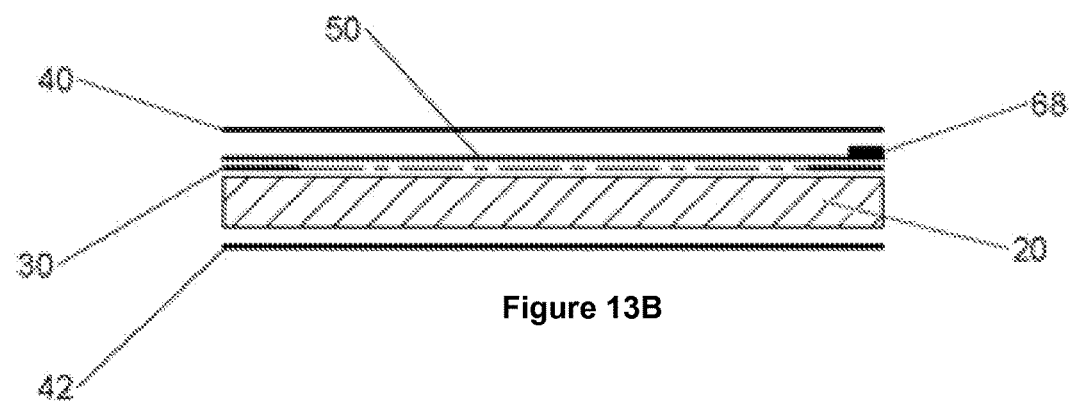

As shown in FIG. 13B, in some embodiments, the grounding electrode 50 is its own layer of material, and there is no heater (e.g., heating element 10). In these cases, the grounding electrode may advantageously be made of a semi-conductive polymer such as polypyrrole because of its flexibility, stretchability, durability, radiolucency and radar-absorbing attributes, compared to other metal coated fabrics.

In certain embodiments of the invention as in FIGS. 13A and 13B, the grounding electrode 50 is electrically connected via an electrical conductor, or bus bar 68. The bus bar 68 of some embodiments of this invention may be attached to the grounding electrode 50 by sewing with electrically conductive thread. This construction maintains flexibility and durability with repeated flexing. The sewn connection between the bus bar 68 and the grounding electrode 68 according to embodiments of the invention results in a connection that is very robust, flexible and tolerant of extreme flexing and resistant to degradation.

According to some embodiments, the bus bar 68 is coupled to the grounding electrode 68 by a stitched coupling, for example, formed with electrically conductive thread such as silver-coated polyester or nylon thread (Marktek Inc., Chesterfield, Mo.), extending through the grounding electrode (e.g., 10 or 50) and through the bus bar 68. Alternative threads or yarns employed by embodiments of the present invention may be made of other polymeric or natural fibers coated with other electrically conductive materials. In addition, nickel, gold, platinum and various conductive polymers can be used to make conductive threads. Metal threads such as stainless steel, copper or nickel could also be used for this application. According to an exemplary embodiment, the bus bar 68 may be comprised of flattened tubes of braided wires; for example, a flat braided silver coated copper wire, and may thus accommodate the attaching thread extending there through, passing through openings between the braided wires thereof. In addition, such bus bars 68 are flexible, thereby enhancing the flexibility of the mattress heater assembly. According to alternate embodiments, the bus bar 68 may be a conductive foil or wire, flattened braided wires not formed in tubes, an embroidery of conductive thread, a printing of conductive ink, or other suitable bus bar construction.

In some embodiments, the dielectric is the outer shell material 40 of the underbody support (mattress overlay or pad 2). In some embodiments, other layers of material such as fabric or foam 74 (FIG. 14) may be interposed between the shell dielectric material 40 and the heater/grounding electrode material 10. In some embodiments, these layers of materials are preferably not laminated together, thereby maintaining maximal flexibility and stretchability for accommodating the patient into the pad 2.

In some embodiments, one or both sides of the grounding electrode layer 10, 50 (and/or heating element 10) is coated on its upper side with a thin layer of flexible, stretchable elastomeric material such as rubber or silicone. This coating of elastomeric material interposed between the electrode and the dielectric material layers serves as second, redundant, safety dielectric layer should an inadvertent hole be put into the outer shell. The redundant dielectric layer would prevent direct electrical coupling between the patient and the grounding electrode material 10, 50, which could cause a burn.

Preferably, the elastomeric material is applied as a gel or liquid so that it can coat the individual fibers of the heating element material (e.g. 310, 502, 10) before it sets up into its elastomeric solid form. Coating the individual fibers maximally protects the heating element, from moisture damage. It also limits the electrical contact area to an inadvertently cut edge in the exceedingly unlikely event that the both the dielectric and heater layers are cut and the active electrode of the electrosurgical unit is inserted into the cut. In this instance the polymeric heaters fibers at the cut edge would melt and retract from the electrode, automatically limiting the adverse current flow.

In some embodiments, the return electrode wire 70 is electrically connected 72 directly to the grounding electrode material 10. Since the grounding electrode 10 is the heating element 10, the electrode itself adds resistance to the current flow through the circuit. The further the current may flow through the heater material, the greater the resistance. A return electrode wire 70 connected 72 to one end of the heating element 10 would create a situation wherein the electrical resistance to current flow would be significantly greater for current originating at the far end compared to the end of the patient closest to the wire connection 72.

In some embodiments, the return electrode wire 70 is electrically connected 72 to one of the bus bars 62, 64. Connecting the return electrode wire 70 to the bus bar 62 or 64 is advantageous when the grounding electrode material is a resistive heating element 10 that adds resistance to the circuit. Since the low resistance bus bar 62, 64 runs substantially parallel to the patient along an edge of the grounding electrode, the resistance to the current flow caused by the heater material is substantially equal along the entire length of the patient that is contacting the grounding electrode creating a safe condition.

In some embodiments, the shared conductive pathway through the heating element 10 involves that the capacitive coupling electrode of the instant invention be adapted to hook to patient warming power supplies and electrosurgical generator that are designed with a "floating" output. By "floating," we mean that the electrical current within each of the respective circuits has no potential or reference with respect to earth (ground) or with respect to the other piece of equipment. This configuration allows simultaneous operation of the patient warming power supply and electrosurgical generator without electrical interference occurring between the two.

In some embodiments, the shared conductive pathway through the heating element 10 may require that the capacitive coupling electrode of the instant invention be adapted to hook only to patient warming power supplies that supply a low voltage direct current (48 volts or less) and an electrosurgical unit that supplies an RF current. This configuration helps to allow simultaneous operation of the patient warming power supply and electrosurgical unit without electrical interference occurring between the two.

In FIGS. 12 and 16, the shell 40, 42 protects and isolates the heater assembly 1 from an external environment of the heater assembly 1 and may further protect a patient disposed on the heated pad 2 from electrical shock hazards. According to preferred embodiments, the shell 40, 42 is waterproof to prevent fluids, for example, bodily fluids, IV fluids, or cleaning fluids, from contacting the heater assembly 1, and may further include an anti-microbial element, such as SILVERion® antimicrobial fabric available from Domestic Fabrics Corporation (Kinston, N.C.), which is extruded in the plastic film of the shell material.

As shown in FIGS. 15 and 16, in some embodiments, a layer of plastic film is placed over each broad surface of the heater assembly 1, as an upper shell 40 and a lower shell 42 but is not bonded to the heater assembly 1. The two layers of plastic film are bonded to each other around a periphery 48 of the heater assembly 1 to form a water-resistant shell. The bond may be from heat, radio frequency (RF), ultrasound, solvent or adhesive, for example. The heater assembly 1 may be "free floating" within the shell with no attachment to the shell, or can be attached to the shell, such as only at the edges of the heater assembly 1 as described above, for example. This bond construction around the periphery 48 of the heated pad 2 creates a durable shell without folds, creases, crevasses or sewing needle holes that can collect infectious debris and be difficult to clean. The heater assembly 1 covered by a shell of plastic film and optionally including a foam or other support layer comprises a heated mattress, mattress overlay, or pad according to some embodiments.

Figure 23:
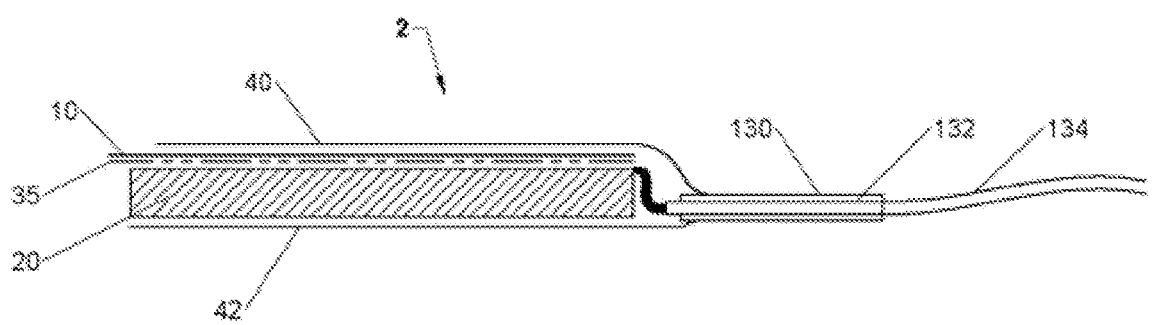
FIG. 23 is a cross sectional view of a heated mattress overlay or pad with a power entry assembly located in the peripheral bond between the shell layers in accordance with embodiments of the invention.

FIG. 23 depicts a cross section of a portion of an alternative embodiment of a heated pad 2, in which the fabric heating element 10 is bonded to an overlaying plastic film layer comprising an upper shell 40 by a layer of adhesive 35. In such embodiments, the upper shell 40 can be stretched and held in position by the compressible material layer 20 or by anchoring the heated pad 2 laterally, with or without bonding the shell 40, 42 to the heating element. When the stretched layer of upper shell material 40 is bonded to the heating element 10, this may reduce or prevent wrinkling or folding of the heater element 10 and yet maintain flexibility and stretchability (depending on the stretchability of the shell material). In the embodiment shown, the heated pad 2 further includes a lower shell 42 beneath the compressible material layer 20.

Figure 24:
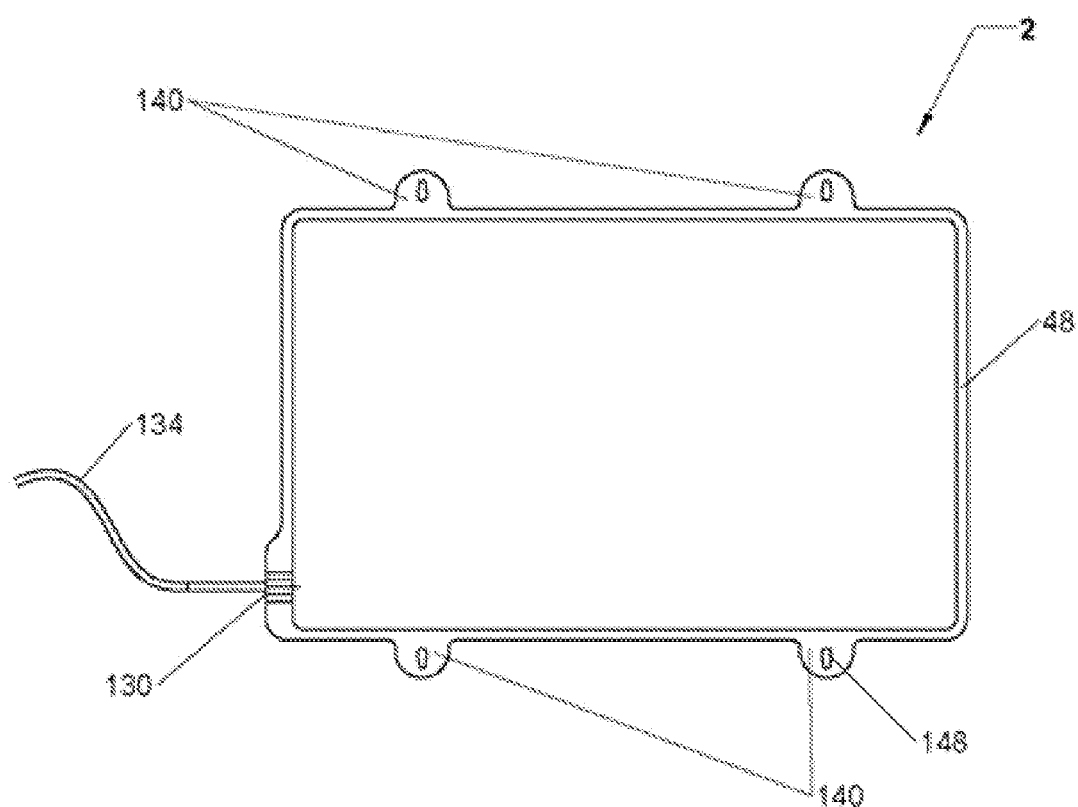
FIG. 24 is an illustration of a heated mattress overlay or pad with attachment tabs in accordance with embodiments of the invention.

In certain embodiments, such as the embodiments shown in FIGS. 23 and 24, the shell construction allows a power entry module 130 to be located and bonded between the shell, such as the layers of plastic film 40, 42, at the edge of the shell within the bonded layers 48. The power entry module 130 can be bonded with adhesive, solvent or heat, for example, between the adjacent layers of upper and lower shell 40, 42. Sewn shell constructions known in the art prevent the power entry from being located at the sewn edge and result in the power entry being located on the flat surface of the shell rather than the edge, which may result in the patient laying on the hard lump created by the power entry module and which could contribute to the formation of a pressure injury. In some embodiments, the power entry module 130 is a piece of molded plastic, for example in a shield-shape, that can be sealed between the sheets 40 and 42 in the peripheral bond 48 edge seal of the shells 40, 42. The pointed ends of the shield-shaped power entry module 130 allows the shells 40, 42 to transition smoothly from the area where the upper and lower shells 40, 42 are sealed to each other, to the adjacent area where the shells 40, 42 are sealed to the power entry module 130 and then back to the shells 40, 42 being sealed to each other. In some embodiments, the power entry module 130 includes a tubular channel 132 traversing from the outer side to the inner side of the shell. The tubular channel 132 may be sized to accommodate a wire cable 134 that contains the power and sensor wires. The wire cable 134 can pass through the tubular channel 132 from the outside to the inside of the heated pad 2 and can be adhesive, solvent or heat bonded to the power entry module in this position, creating a watertight seal. In another embodiment, the power entry module 130 may be shaped and sized to house a plug-in connector. In some embodiments, the return electrode wire 70 that connects to the electrosurgical generator can pass through an identical tubular channel 132 from the inside to the outside of the heated pad 2 as the power entry module 130, which is used for the power cable 134 to exit the shell.

The heated underbody support may have two or more attachment points such as tabs 140 for securing the support over the top of a surgical mattress or table such as is shown in FIG. 23. These attachment points may be tabs 140 or flaps made from shell material that extend outward from the peripheral bond 48 of the shell. These attachment points may be fiber-reinforced and yet flexible and somewhat loose, so that they do not cause hammocking of the shell. The attachment points can be secured to the table with many different means including straps, ties, loops, hooks, snaps, barbs, Velcro or other attachment means.

The heater assembly 1 of these inventions can be encased in a shell of plastic film as described, or may have no shell. With or without a shell or compressible material layer 20, it can be used alone, or it can be used as a mattress overlay on top of, or can be inserted into, a pressure reducing mattress. For example, since pressure reducing mattresses typically have water resistant covers, the heater assembly 1 may be inserted directly into the mattress, inside the mattress cover, without a shell on the heater assembly 1. In either case, the heater assembly 1, or heated pad 2 is designed to have little or no negative impact on the pressure reducing capabilities of the mattress on which it is laying or into which it is inserted.

The heated pad 2 may have two or more attachment points such as tabs 140 for securing the support over the top of a surgical mattress or table such as is shown in FIG. 24. These attachment points may be tabs 140 or flaps made from shell material that extend outward from the peripheral bond 48 of the shell. These attachment points may be fiber-reinforced and yet flexible and somewhat loose, so that they do not cause hammocking of the shell. The attachment points can be secured to the table with many different means including straps, ties, loops, hooks, snaps, barbs, Velcro or other attachment means.

The shell of the heater assembly 1 is preferably water resistant, flexible, and durable enough to withstand the wear and tear of operating room use. Examples of materials which may be used for the shell include urethane and PVC. Many other suitable plastic film or fiber-reinforced plastic film shell materials are anticipated. In some embodiments, the shell material is about 0.010-0.015 inch thick. In this thickness range, both urethane and PVC, for example, are strong but retain an adequate stretchability. The heated pad 2 may cover approximately the entire surface of the surgical table or any other bed. Alternately, the heated pad 2 may be sized to fit some or all of the cushion that form the support surface of a surgical table. For example, if the cushion has multiple separate sections, such as three, the heated pad 2 may be sized to fit over one or two or all three of the cushion sections.

Figure 25:
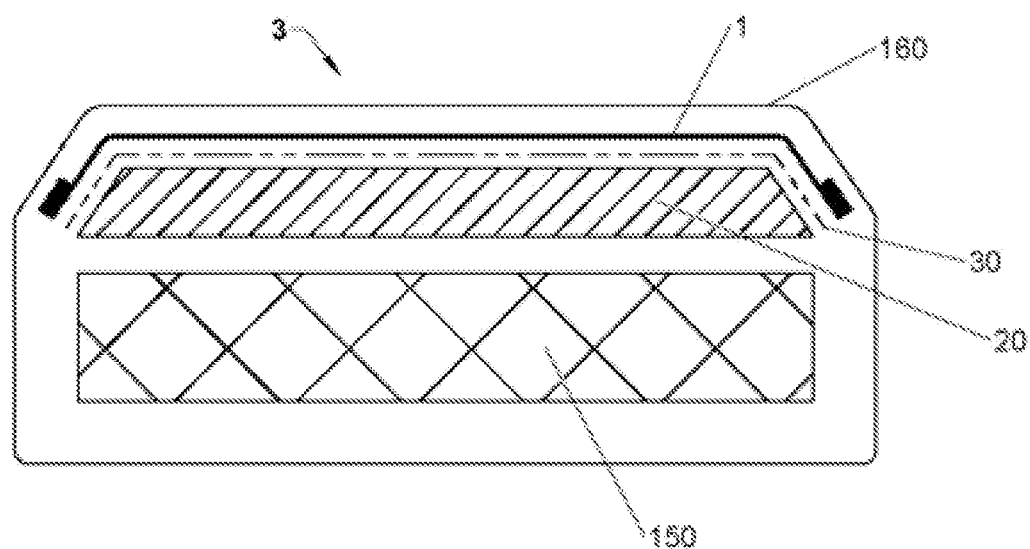
FIG. 25 is a cross sectional view of a heated mattress including a visco-elastic foam layer in accordance with embodiments of the invention.

As shown in FIG. 25, in some embodiments, compressible material layer 20 or a foam layer 150 may be high tech foam to reduce the pressure exerted against the patient's skin during surgery. High tech foams include but are not limited to visco-elastic foams that are designed to maximize accommodation of the patient into the mattress (e.g., pad). As previously noted, accommodation refers to the sinking of the user, such as the patient, into the pad 2 until a maximal amount of support surface area is in contact with a maximal amount of skin surface, and the pressure exerted across the skin surface is as uniform as possible. These high tech foam materials may accommodate the patient more effectively than simple urethane upholstery foam. Unlike other mattress heaters or heating materials, the unique stretchable, flexible, free floating design of the heater assemblies 1 described herein allow them to overlay a layer of visco-elastic foam and maintain the accommodation properties of the foam. Further, the heater assembly 1 of this invention is soft, flexible and stretchable enough to be the separated from the patient by only a single layer of plastic film and still be comfortable. The avoidance of multiple layers of materials interposed between the patient and the mattress foam maximizes accommodation and heat transfer.

In embodiments comprising heated mattresses 3 including foam layers 150, a water-resistant shell or cover 160 may encase the foam 150 as shown, for example, in FIG. 25. The foam 150 may be simple urethane foam or high-tech foam such as visco-elastic foam, for example. The cover 160 may be made of plastic film that has been extruded onto a woven fabric (e.g., Naugahyde), for example. In one embodiment, the heater assembly 1 may be located within or may be removably inserted directly into the mattress cover 160, with or without a shell 40 on the heater assembly 1. The heater assembly 1 may be placed directly on top of the mattress foam 150 inside the cover 160 or a heater assembly 1 (with its own shell) may be placed on top of a mattress outside of the mattress cover 160. If a foam mattress has its own shell, the thickness of the shell 40 of the heater assembly 1 can be reduced to, for example, about 0.003 and about 0.010 inch, or even omitted, because the heater assembly 1 is protected from mechanical damage by the cover 160 of the mattress 150. The thinner shell material improves the stretch-ability of the shell. Alternately, the heating element 10 may be bonded directly to the mattress foam 150.

The thermal effectiveness of this heated underbody support can be optimized when the heating element 10 is overlaying a layer that can provide maximal accommodation of the patient positioned on the support. In this condition, the heating element 10 is in contact with a maximal amount of the patient's skin surface which maximizes heat transfer. Heated pads made with inflatable air chambers forming or included in the compressible material layer 20 or in addition to the compressible material layer 20, can provide excellent accommodation. Further, a heated underbody support with excellent accommodation properties having a heating element 10 as described herein avoids degrading the accommodation properties of the mattress when a heater assembly 1 is added.

In the foregoing detailed description, the invention has been described with reference to specific embodiments. However, it may be appreciated that various modifications, changes and alternative combinations can be made without departing from the scope of the invention as set forth in the appended claims. Although embodiments of the invention are described in the context of a hospital operating room, it is contemplated that some embodiments of the invention may be used in other environments. Those embodiments of the present invention, which are not intended for use in an operating environment and need not meet stringent FDA requirements for repeated used in an operating environment, need not including particular features described herein, for example, related to precise temperature control. Thus, some of the features of preferred embodiments described herein are not necessarily included in preferred embodiments of the invention which are intended for alternative uses.

The invention claimed is:

1. An electric heating pad for warming a patient comprising a heated underbody support, heated mattress or heated mattress overlay comprising:
    a flexible sheet-like heating element including an upper edge, a lower edge, and at least two side edges;
    a shell covering the heating element and comprising at least two sheets of flexible material; and
    a weld coupling the two sheets of flexible material together about the edges of the heating element, wherein the weld is one of a RF weld, ultrasonic weld, or a heat bond,
    wherein the two sheets comprise a weldable polymeric layer to facilitate the one of the RF weld, the ultrasonic weld, or the heat bond,
    wherein at least a portion of the heating pad is flexible to substantially conform to curves of the patient, and
    wherein the at least two sheets of flexible material comprise a first sheet that is configured to be in contact with the patient during warming, and a second sheet that is configured to be spaced apart from the patient during warming, and a layer of thermally insulating polymeric foam is positioned between the heating element and the second sheet of the shell,
    wherein a thin layer of thermally insulating material is positioned between the heating element and the patient-contacting surface of the shell.

2. The electric heated underbody support, heated mattress or heated mattress overlay of claim 1, wherein the layer of thermally insulating polymeric foam is laminated to the heating element with adhesive.

3. The electric heated underbody support, heated mattress or heated mattress overlay of claim 1, wherein the layer of thermally insulating material is polymeric foam.

4. The electric heated underbody support, heated mattress or heated mattress overlay of claim 1, wherein the layer of thermally insulating material is fabric.

5. The electric heated underbody support, heated mattress or heated mattress overlay of claim 1, wherein the two sheets further comprise at least one strap.

6. The electric heated underbody support, heated mattress or heated mattress overlay of claim 5, wherein the at least one strap protrudes from the edges of the sheets of flexible material.

7. The electric heated underbody support, heated mattress or heated mattress overlay of claim 6, wherein the at least one strap protrudes from the edges of the sheets of flexible material and is included in the weld such that there is no seam joining the straps with the sheets.

8. The electric heated underbody support, heated mattress or heated mattress overlay of claim 5, wherein the at least one strap comprises a reinforcing layer of material interposed between the two sheets of flexible material.

9. The electric heated underbody support, heated mattress or heated mattress overlay of claim 1, further comprising a catalyst to accelerate hydrogen peroxide decomposition coated on or impregnated into an element within the shell, or on the interior surface of the shell.

10. The electric heated underbody support, heated mattress or heated mattress overlay of claim 9, wherein the catalyst to accelerate hydrogen peroxide decomposition comprises manganese dioxide.

11. The electric heated underbody support, heated mattress or heated mattress overlay of claim 9, wherein the catalyst to accelerate hydrogen peroxide decomposition comprises at least one of silver, platinum, transition metal salts, or a combination thereof.

12. The electric heated underbody support, heated mattress or heated mattress overlay of claim 9, wherein when the support, mattress or mattress overlay is exposed to hydrogen peroxide vapor, the catalyst to accelerate hydrogen peroxide decomposition breaks down at least some of the hydrogen peroxide vapor into water and oxygen to decrease hydrogen peroxide corrosion of the electrical components.

13. The electric heated underbody support, heated mattress or heated mattress overlay of claim 9, wherein when the catalyst to accelerate hydrogen peroxide decomposition coating or impregnation comprises a binding material.

14. The electric heated underbody support, heated mattress or heated mattress overlay of claim 13, wherein the binding material comprises methyl cellulose.

15. An electric heating pad for warming a patient comprising a heated underbody support, heated mattress or heated mattress overlay comprising:
a flexible sheet-like heating element including an upper edge, a lower edge, and at least two side edges;
a shell covering the heating element and comprising at least two sheets of flexible material; and
a weld coupling the two sheets of flexible material together about the edges of the heating element, wherein the weld is one of a RF weld, ultrasonic weld, or a heat bond,
wherein the two sheets comprise a weldable polymeric layer to facilitate the one of the RF weld, the ultrasonic weld, or the heat bond,
wherein at least a portion of the heating pad is flexible to substantially conform to curves of the patient, and
wherein the heating element has a surface area of generally uniform electrical resistance per unit area such that the heating element produces a substantially uniform watt density output across the surface area when the element is electrically powered, and
further comprising:
a temperature sensor coupled to the heating element at a first location thereof where the heating element is configured and located to be in conductive contact with the body of the patient during warming, the first location defining a first temperature zone of the surface area of the element;
a temperature controller coupled to the temperature sensor; and
an electric power source coupled to the heating element and to the temperature controller, the power source being controlled by the controller, according to a sensed temperature of the first temperature zone, as sensed by the temperature sensor, in order to maintain a first temperature of the first temperature zone lower than a second temperature of a second temperature zone of the surface area of the heating element, the second temperature zone being defined by a second location of the heating element that is not in conductive contact with the body during warming.

16. The electric heated underbody support, heated mattress or heated mattress overlay of claim 15, wherein the at least two sheets of flexible material comprise a first sheet that is configured to be in contact with the patient during warming, and a second sheet that is configured to be spaced apart from the patient during warming, and wherein a layer of thermally insulating polymeric foam is positioned between the heating element and the surface of the second sheet of the shell.

17. The electric heated underbody support, heated mattress or heated mattress overlay of claim 16, wherein the layer of thermally insulating polymeric foam is laminated to the heating element with adhesive.

18. The electric heated underbody support, heated mattress or heated mattress overlay of claim 16, wherein a thin layer of thermally insulating material is positioned between the heating element and the second sheet of the shell.

19. The electric heated underbody support, heated mattress or heated mattress overlay of claim 18, wherein the layer of thermally insulating material is polymeric foam.

20. The electric heated underbody support, heated mattress or heated mattress overlay of claim 18, wherein the layer of thermally insulating material is fabric.

21. The electric heated underbody support, heated mattress or heated mattress overlay of claim 18, wherein the layer of thermally insulating material is laminated to the heating element with adhesive.

22. The electric heated underbody support, heated mattress or heated mattress overlay of claim 15, wherein the at least one strap protrudes from the edges of the sheets of flexible material.

23. The electric heated underbody support, heated mattress or heated mattress overlay of claim 22, wherein the at least one strap protrudes from the edges of the sheets of flexible material and is included in the weld such that there is no seam joining the straps with the sheets.

24. The electric heated underbody support, heated mattress or heated mattress overlay of claim 15, wherein the at least one strap comprises a reinforcing layer of material interposed between the two sheets of flexible material.

25. The electric heated underbody support, heated mattress or heated mattress overlay of claim 15, wherein the flexible heating element conforms to the contours of the body of the patient.

26. The electric heated underbody support, heated mattress or heated mattress overlay of claim 15, wherein, in response to pressure, the flexible heating element is adapted to stretch into a 3-dimentional compound curve without wrinkling or folding while maintaining electrical conductivity, and wherein the heating element is adapted to return to the planar shape when pressure is removed.

27. The electric heated underbody support, heated mattress or heated mattress overlay of claim 15, further comprising:
   a first conductive bus bar coupled to the heating element and extending alongside a first edge of the heating element, the first bus bar being adapted for coupling to a power source for powering the heating element;
   a second conductive bus bar coupled to the heating element and extending alongside a second edge of the heating element, the second bus bar being adapted for coupling to the power source for powering the heating element;
   the heating element is stitched to the first bus bar with a first row of electrically conductive stitching; and
   the heating element is stitched to the second bus bar with a second row of electrically conductive stitching.

28. The electric heated underbody support, heated mattress or heated mattress overlay of claim 27, further comprising:
   a first electrically insulating member interposed between the first conductive bus bar and the flexible heater and being secured therebetween by the first row of conductive stitching, the first electrically insulating member preventing direct electrical contact between the first conductive bus bar and the flexible heater; and
   a second electrically insulating member interposed between the second conductive bus bar and the flexible heater and being secured therebetween by the second row of electrically conductive stitching, the second electrically insulating member preventing direct electrical contact between the first conductive bus bar and the flexible heater.

29. The electric heated underbody support, heated mattress or heated mattress overlay of claim 15, further comprising at least one securing strip coupled to the heating element, the at least one securing strip being coupled to the shell by the thermal bond.

30. An electric heating pad for warming a patient comprising a heated underbody support, heated mattress or heated mattress overlay comprising:
   a flexible sheet-like heating element including an upper edge, a lower edge, and at least two side edges;
   a shell covering the heating element and comprising at least two sheets of flexible material;
   a catalyst to accelerate hydrogen peroxide decomposition coated on or impregnated into an element within the shell, or on the interior surface of the shell;
   a weld coupling the two sheets of flexible material together about the edges of the heating element, wherein the weld is one of a RF weld, ultrasonic weld, or a heat bond; and
   a flexible insulating layer extending over a side of the heating element and covered by the shell,
   wherein at least a portion of the heating pad is flexible to substantially conform to curves of the patient, and
   wherein, in response to pressure, the flexible heating element is adapted to stretch into a 3-dimentional compound curve without wrinkling or folding while maintaining electrical conductivity, and wherein the heating element is adapted to return to the planar shape when pressure is removed.

31. The electric heated underbody support, heated mattress or heated mattress overlay of claim 30, wherein the layer of thermally insulating polymeric foam is laminated to the heating element with adhesive.

32. The electric heated underbody support, heated mattress or heated mattress overlay of claim 30, wherein the insulating layer comprises one of a foam, a high loft non-woven fibrous material, a low loft non-woven fibrous material, a woven fabric, such as cotton or fiberglass, a thin plastic film, cotton, a non-flammable material, cotton and fiberglass.

33. The electric heated underbody support, heated mattress or heated mattress overlay of claim 30, wherein the heating element comprises a nonconductive layer coated with a conductive material.

34. The electric heated underbody support, heated mattress or heated mattress overlay of claim 33, wherein the nonconductive layer of the flexible heater comprises a woven polymer and the conductive material comprises one of: polypyrrole, carbonized ink and metalized ink.

35. The electric heated underbody support, heated mattress or heated mattress overlay of claim 33, wherein the nonconductive layer of the flexible heating element comprises a non-woven polymer and the conductive material comprises one of: polypyrrole, carbonized ink and metalized ink.

36. The electric heated underbody support, heated mattress or heated mattress overlay of claim 30, wherein the catalyst to accelerate hydrogen peroxide decomposition comprises manganese dioxide.

37. The electric heated underbody support, heated mattress or heated mattress overlay of claim 30, wherein the catalyst to accelerate hydrogen peroxide decomposition comprises at least one of silver, platinum, transition metal salts, or a combination thereof.

38. The electric heated underbody support, heated mattress or heated mattress overlay of claim 30, wherein when the support, mattress or mattress overlay is exposed to hydrogen peroxide vapor, the catalyst to accelerate hydrogen peroxide decomposition breaks down at least some of the hydrogen peroxide vapor into water and oxygen to decrease hydrogen peroxide corrosion of the electrical components.

39. The electric heated underbody support, heated mattress or heated mattress overlay of claim 30, wherein when the catalyst to accelerate hydrogen peroxide decomposition coating or impregnation comprises a binding material.

40. The electric heated underbody support, heated mattress or heated mattress overlay of claim 39, wherein the binding material comprises methyl cellulose.

41. An electric heating pad for warming a patient comprising a heated underbody support, heated mattress or heated mattress overlay comprising:
   a flexible sheet-like heating element including an upper edge, a lower edge, and at least two side edges;
   a shell covering the heating element and comprising at least two sheets of flexible material; and
   a weld coupling the two sheets of flexible material together about the edges of the heating element, wherein the weld is one of a RF weld, ultrasonic weld, or a heat bond,
   wherein the two sheets comprise a weldable polymeric layer to facilitate the one of the RF weld, the ultrasonic weld, or the heat bond, wherein at least a portion of the heating pad is flexible to substantially conform to curves of the patient, and further comprising a catalyst to accelerate hydrogen peroxide decomposition coated on or impregnated into an element within the shell, or on the interior surface of the shell.

42. The electric heated underbody support, heated mattress or heated mattress overlay of claim 41, wherein the catalyst to accelerate hydrogen peroxide decomposition comprises manganese dioxide.

43. The electric heated underbody support, heated mattress or heated mattress overlay of claim 41, wherein the catalyst to accelerate hydrogen peroxide decomposition comprises at least one of silver, platinum, transition metal salts, or a combination thereof.

44. The electric heated underbody support, heated mattress or heated mattress overlay of claim 41, wherein when the support, mattress or mattress overlay is exposed to hydrogen peroxide vapor, the catalyst to accelerate hydrogen peroxide decomposition breaks down at least some of the hydrogen peroxide vapor into water and oxygen to decrease hydrogen peroxide corrosion of the electrical components.

45. The electric heated underbody support, heated mattress or heated mattress overlay of claim 41, wherein when the catalyst to accelerate hydrogen peroxide decomposition coating or impregnation comprises a binding material.

46. The electric heated underbody support, heated mattress or heated mattress overlay of claim 41, wherein the binding material comprises methyl cellulose.

47. The electric heated underbody support, heated mattress or heated mattress overlay of claim 30, wherein the flexible insulating layer is a layer of thermally insulating polymeric foam that positioned between the heating element and the surface of the shell that does not contact the patient.

* * * * *

UNITED STATES PATENT AND TRADEMARK OFFICE
CERTIFICATE OF CORRECTION

PATENT NO. : 10,201,935 B2  
APPLICATION NO. : 14/842533  
DATED : February 12, 2019  
INVENTOR(S) : Scott D. Augustine et al.

Page 1 of 1

It is certified that error appears in the above-identified patent and that said Letters Patent is hereby corrected as shown below:

On the Title Page

Column 1, on the first line of Item (63), delete "Continuation" and insert --Continuation-in-part--.

Signed and Sealed this  
Ninth Day of July, 2019

Andrei Iancu  
*Director of the United States Patent and Trademark Office*